US010881849B2

(12) United States Patent
Pisarev et al.

(10) Patent No.: US 10,881,849 B2
(45) Date of Patent: Jan. 5, 2021

(54) COMPACT MUSCLE STIMULATOR

(71) Applicant: POWERDOT, INC., Carlsbad, CA (US)

(72) Inventors: Alexey Pisarev, Singapore (SG); Vladimir Pisarev, Moscow (RU)

(73) Assignee: POWERDOT, INC., Carlsbad, CA (US)

( * ) Notice: Subject to any disclaimer, the term of this patent is extended or adjusted under 35 U.S.C. 154(b) by 145 days.

(21) Appl. No.: 16/087,447

(22) PCT Filed: Mar. 22, 2017

(86) PCT No.: PCT/IB2017/000383
§ 371 (c)(1),
(2) Date: Sep. 21, 2018

(87) PCT Pub. No.: WO2017/163131
PCT Pub. Date: Sep. 28, 2017

(65) Prior Publication Data
US 2019/0167973 A1 Jun. 6, 2019

Related U.S. Application Data

(60) Provisional application No. 62/311,811, filed on Mar. 22, 2016, provisional application No. 62/366,299, filed on Jul. 25, 2016.

(51) Int. Cl.
*A61N 1/04* (2006.01)
*A61B 5/11* (2006.01)
(Continued)

(52) U.S. Cl.
CPC .......... *A61N 1/0452* (2013.01); *A61B 5/0488* (2013.01); *A61B 5/11* (2013.01);
(Continued)

(58) Field of Classification Search
CPC .............. A61N 1/0452; A61N 1/36031; A61N 1/36003; A61N 1/37247; A61B 5/4519; A61B 5/11; A61B 5/0488
(Continued)

(56) References Cited

U.S. PATENT DOCUMENTS 5,507,788 A * 4/1996 Lieber ................ A61N 1/36003
607/48
5,836,995 A * 11/1998 MGraw .............. A61N 1/36014
607/48
(Continued)

FOREIGN PATENT DOCUMENTS

WO 2010/003106 A2 1/2010
WO WO2014194200 A1 * 12/2014 ................ A61N 1/36
WO WO2017023864 A1 * 2/2017 ................ A61N 1/36

OTHER PUBLICATIONS

International Search Report dated Jul. 25, 2017 in PCT/IB2017/000383 (8 pages).
(Continued)

*Primary Examiner* — Nathan J Jenness
(74) *Attorney, Agent, or Firm* — Northstar Law Group; Thomas J. Bassolino

(57) ABSTRACT

Systems, methods, and devices are provided herein providing electrical muscle stimulation (EMS). In some instances, an EMS device may be provided. The EMS device may be compact, light, and unobtrusive such that it can be used by a person going about his or her daily activities. In some instances, the EMS device may comprise additional sensors for increased functionality and may be capable of interacting with additional devices or platforms to provide a full-fledged EMS device capability.

20 Claims, 15 Drawing Sheets

(51) Int. Cl.
*A61B 5/00* (2006.01)
*A61N 1/36* (2006.01)
*A61N 1/372* (2006.01)
*A61B 5/02* (2006.01)
*A61B 5/0488* (2006.01)
*A61B 5/103* (2006.01)

(52) U.S. Cl.
CPC ........ *A61B 5/4519* (2013.01); *A61N 1/36003* (2013.01); *A61N 1/36031* (2017.08); *A61B 5/02* (2013.01); *A61B 5/103* (2013.01); *A61N 1/37247* (2013.01); *A61N 1/37282* (2013.01)

(58) Field of Classification Search
USPC .......................................................... 607/48
See application file for complete search history.

(56) References Cited

U.S. PATENT DOCUMENTS

| | | |
|---|---|---|
| 5,961,542 A | 10/1999 | Agarwala |
| 3,041,259 A | 3/2000 | Agarwala et al. |
| 6,324,432 B1 | 11/2001 | Rigaux et al. |
| 8,452,409 B2 | 5/2013 | Bachinski et al. |
| 8,565,888 B2 | 10/2013 | Buhlmann et al. |
| 8,977,366 B2 | 3/2015 | Bachinski et al. |
| 9,044,587 B2 | 6/2015 | Bachinski et al. |
| 9,144,688 B2 | 9/2015 | Baumgartner et al. |
| 9,220,896 B2 | 12/2015 | Bachinski et al. |
| 9,242,091 B2 | 1/2016 | Bachinski et al. |
| 2003/0195587 A1 | 10/2003 | Rigaux et al. |
| 2009/0228068 A1 | 9/2009 | Buhlmann et al. |
| 2013/0123568 A1 | 5/2013 | Hamilton et al. |
| 2014/0031910 A1* | 1/2014 | Fisher ................ A61N 1/36003 607/118 |
| 2014/0188188 A1 | 7/2014 | Choi et al. |
| 2014/0249601 A1 | 9/2014 | Bachinski et al. |
| 2014/0371814 A1* | 12/2014 | Spizzirri .............. A61N 1/0452 607/48 |
| 2015/0075697 A1 | 3/2015 | Gildersleeve |
| 2015/0151124 A1 | 6/2015 | Mueller et al. |
| 2015/0182752 A1 | 7/2015 | Buhlmann et al. |
| 2016/0045721 A1 | 2/2016 | Bachinski |
| 2016/0066626 A1 | 3/2016 | Gildersleeve |
| 2016/0074658 A1 | 3/2016 | Bachinski et al. |
| 2016/0082273 A1 | 3/2016 | Baumgartner et al. |

OTHER PUBLICATIONS

Written Opinion dated Jul. 25, 2017 in PCT/IB2017/000383 (7 pages).

* cited by examiner

COMPACT MUSCLE STIMULATOR

CROSS-REFERENCE

The present application is filed under 35 U.S.C. § 371 as the U.S. national phase of International Patent Application No. PCT/IB2017/000383, filed Mar. 22, 2017, which designated the United States and claims priority to U.S. Provisional Patent Application No. 62/311,811, filed on Mar. 22, 2016, and U.S. Provisional Patent Application No. 62/366,299, filed on Jul. 25, 2016, each of which is entirely incorporated herein by reference.

BACKGROUND

Electrical stimulation devices have a wide range of real world applications including uses in treatment, therapy, relaxation, fitness, athletic performance enhancement, entertainment, and the like. For example, electrodes may be attached to a user and the electrical stimulation device may transmit impulses to the user to stimulate and engage muscle(s) of the user, e.g., as during a workout. While offering a plurality of benefits, use of the electrical stimulation devices have been limited, for example, due to unwieldiness, difficulty of operation, and/or limited functionalities.

SUMMARY

The present disclosure provides full-fledged electrical stimulation devices, systems and methods that can be used by various users, including users not having expertise to operate such devices and systems.

Presently, electric stimulation devices, also referred to herein as electrical stimulation devices and/or electrical muscle stimulation (EMS) devices, may utilize a main body (e.g., where electrical impulses are generated) and a plurality of electrodes coupled to the main body. In some instances, EMS devices with full functionality able to perform various stimulation sessions (e.g., simultaneously or in sequence) may comprise a main body that is bulky or unwieldy and not be suited for everyday use. Portable EMS devices may still lack a main body that is suited for integration into everyday use. For example, the portable EMS device may have a main body with various controls meant to be handled and adjusted by the user. Alternatively or in addition, the portable EMS device may lack ability to perform a wide variety of stimulation sessions simultaneously or in sequence and may be limited in its functionality and/or application.

Accordingly, recognized herein is the need for full-fledged EMS device that can be integrated into everyday use. An EMS device with a sleek profile may be provided. The EMS device may be portable. The EMS device may be attached to the user for extended periods of time and may be small in its profile such that it may be worn under clothes, e.g., to allow multitasking or for everyday use. The EMS device may additionally comprise various sensors on or within the device. In some instances, the EMS device may be provided with inter-device connectivity such that a plurality of the EMS devices can provide stimulation sessions that are varied or expansive in scope. The EMS device may additionally utilize a platform for managing or recording stimulation sessions.

Thus, in one aspect, an electric stimulation device for stimulating a user may be provided. The device comprises: a central body comprising: a sensor configured to sense one or more signals from the user; a processing unit configured to (i) execute a stimulation program, and (ii) use the sensor to detect the one or more signals from the user; and a pulse generator operatively coupled to the processing unit, wherein the pulse generator is configured to generate electrical impulses in response to the stimulation program; and one or more pads in electrical communication with the pulse generator in the central body, wherein the one or more pads are configured for attachment to the user, and wherein the one or more pads are configured to transmit the electrical pulses to stimulate the user in accordance with the stimulation program.

In some embodiments, the processing unit of the central body is further configured to analyze the sensed signals. In some embodiments, the analysis relates to a gait or hand grip analysis. Optionally, the processing unit of the central body is configured to stimulate the user and analyze the sensed signals simultaneously or sequentially.

In some embodiments, the signals sensed by the sensor system are mechanomyography (MMG) readings. Optionally, the sensor system comprises an accelerometer or a gyroscope. In some embodiments, the MMG readings are further utilized in detection of muscle performance parameters. In some embodiments, the MMG readings are further utilized in detecting a level of muscle fatigue.

In some embodiments, the device is configured to be removably attached to a base unit. In some embodiments, the base unit comprises different types of base units configured for attachment to different targets. Optionally, the different targets comprise a knee, thigh, or forearm of the user. In some embodiments, the base unit comprises one or more straps. In some embodiments, the base unit comprises adhesives.

In some embodiments, the processing unit of the central body is configured to execute a plurality of different stimulation programs. Optionally, the plurality of different stimulation programs are user configurable. In some embodiments, the plurality of different stimulation program differs in at least one of a stimulation frequency, pulse width, duty cycle parameters, ramp up and down values, burst pulse parameters, waveform shape, or interphase interval. In some embodiments, the plurality of different stimulation programs comprise a drop foot assistance program, rehabilitation program, recovery program, relaxation program, or improved performance program.

In some embodiments, the central body has a maximum dimension equal to or less than 10 cm. In some embodiments, the central body has a weight equal to or less than 30 gr.

In some embodiments, the device is configured to be in communication with a mobile device. In some embodiments, the stimulation program is uploaded from the mobile device. In some embodiments, the central body interfaces with the one or more pads via wired connection.

In some embodiments, the device may be provided in a kit for stimulating a user. The kit may comprise: any one of the devices described herein; and instructions for appropriately placing the device on the user. In some embodiments, the instructions comprise a plurality of different appropriate placements of the device depending on a user's needs. In some embodiments, the plurality of different appropriate placements comprise placement of the device on a knee, thigh, or forearm of the user.

In some embodiments, the device may be provided in a kit for stimulating a user. The kit may comprise any one of the devices described herein; and instructions for selecting a stimulation program and appropriately placing the device in correspondence with the stimulation program. In some embodiments, the stimulation program is a drop foot assistance program and the appropriate placement of the device is on or near a peroneal nerve or calf muscle of the user. In some embodiments, the stimulation program is a thigh rehab program and the appropriate placement of the device is on a quad or hamstring muscle of the user. In some embodiments, the stimulation program is a hand rehab program and the appropriate placement of the device is on a forearm of the user.

In another aspect, a system for stimulating a user is provided. The system comprises: a mobile device, at which the user selects a stimulation program; a central body, at which the stimulation program is received, the central body comprising: a sensor configured to sense one or more signals from the user; a processing unit configured to (i) execute the stimulation program, and (ii) use the sensor to detect the one or more signals from the user; and a pulse generator operatively coupled to the processing unit, wherein the pulse generator is configured to generate electrical impulses in response to the stimulation program; and one or more pads in electrical communication with the pulse generator in the central body, wherein the one or more pads are configured for attachment to the user, and wherein the one or more pads are configured to use the electrical pulses to stimulate the user in accordance with the stimulation program.

In another aspect, a method for stimulating a user is provided. The method comprises: receiving, at a central body, a stimulation program from a mobile device, wherein the central body comprises a sensor system configured to sense signals; executing, at a processing unit of the central body, the stimulation program; generating, at a pulse generator operatively coupled to the processing unit, electrical impulses in response to the stimulation program; and transmitting, at one or more pads 1) configured to be attached to the user, and 2) in communication with the central body, the electrical pulses to stimulate the user in accordance with the stimulation program.

In another aspect, an electric stimulation device for stimulating a user is provided. The device comprises: a central body comprising: a processing unit configured to execute a stimulation program; and a pulse generator operatively coupled to the processing unit, wherein the pulse generator is configured to generate electrical impulses in response to the stimulation program, wherein the central body is configured to 1) broadcast a command over a communication channel, and 2) communicate with one or more other bodies substantially similar to the central body, the one or more other bodies configured to receive the broadcast command over the communication channel and generate electrical impulses in response; and one or more pads in communication with the central body or the one or more other bodies, wherein the one or more pads are configured to be attached to the user and transmit the electrical pulses to stimulate the user in accordance with the stimulation program.

In some embodiments, each of the one or more other bodies are substantially similar in shape or size to the central body. Alternatively or in addition, the each of the one or more other bodies comprise internal electrical components substantially similar to that of the central body.

In some embodiments, the central body is configured to broadcast the command over the communication channel as a result of executing the stimulation program.

In some embodiments, the device is configured to be in communication with a mobile device. In some embodiments, the one or more other processing bodies are not in direct communication with the mobile device. In some embodiments, the stimulation program is uploaded from the mobile device.

In some embodiments, the central body is configured to be placed on a first location on the user and wherein the one or more other processing bodies are configured to be placed on different locations on the user. Optionally, the communication channel utilizes a radio-frequency (RF) protocol. The RF protocol may be an ANT+ protocol, Gazell protocol, or Bluetooth Low Energy protocol.

In some embodiments, the one or more other bodies comprise two or more bodies. In some embodiments, a subset of the two or more bodies are utilized in a single stimulation program.

In some embodiments, the central body is configured to execute a plurality of stimulation programs simultaneously. In some embodiments, different subsets of the one or more other bodies execute different stimulation programs simultaneously.

In some embodiments, the central body is configured to be removably attached to a base unit. In some embodiments, the base unit comprises different types of base units configured for attachment to different targets. In some embodiments, the different targets comprise a knee, thigh, or forearm of the user. In some embodiments, the base unit comprises one or more straps. In some embodiments, the base unit comprises adhesives.

In some embodiments, the processing unit is configured to execute a plurality of different stimulation programs. In some embodiments, the plurality of different stimulation programs are user configurable. In some embodiments, the plurality of different stimulation program differs in at least one of a stimulation frequency, pulse width, duty cycle parameters, ramp up and down values, burst pulse parameters, waveform shape, or interphase interval. In some embodiments, the plurality of different stimulation programs comprise a drop foot assistance program, rehabilitation program, recovery program, relaxation program, or improved performance program.

In some embodiments, the central body has a maximum dimension equal to or less than 10 cm. In some embodiments, the central body has a weight equal to or less than 30 gr.

In some embodiments, the device is configured to be in communication with a mobile device. In some embodiments, the stimulation program is uploaded from the mobile device.

In some embodiments, the central body interfaces with the one or more pads via wired connection.

In some embodiments, a kit for stimulating a user is provided. The kit comprises any one of the devices described herein; and instructions for appropriately placing two or more of the device on the user.

In another aspect, a system for stimulating a user is provided. The system comprises: a first central body comprising: a processing unit configured to execute a stimulation program; and a pulse generator operatively coupled to the processing unit, wherein the pulse generator is configured to generate a first set of electrical impulses in response to the stimulation program, wherein the first central body is configured to broadcast a command over a communication channel; a second central body substantially similar to the first central body, wherein the second central body is configured to receive the broadcast command over the communication channel and generate electrical impulses in response; and one or more pads in communication with the first central body or the second central body, wherein the one or more pads are configured to be attached to the user and transmit the electrical pulses to stimulate the user in accordance with the stimulation program.

In another aspect, a method for stimulating a user is provided. The method comprises: placing a first central body on a first location on the user; placing a second central body on a second location on the user, wherein the second central body is substantially similar to the first central body; executing a stimulation program with aid of a processing unit on board the first central body; broadcasting, with aid of the first central body, a command over a communication channel; receiving, at the second central body, the command; generating electrical impulses in response to the stimulation program with aid of a pulse generator; and transmitting the electrical pulses onto the user with aid of one or more pads to stimulate the user in accordance with the stimulation program.

In another aspect, a system for tracking and updating stimulation sessions is provided. The system comprises: a server configured to provide one or more stimulation programs; a mobile device configured to receive the one or more stimulation programs from the server; an electric stimulation device comprising: a central body configured to 1) receive the stimulation program from the mobile device, 2) execute the stimulation program, and 3) generate electrical pulses; and one or more pads in communication with the central body, the one or more pads configured to a) be attached to the user, and b) use the electrical pulses to stimulate the user in accordance with the one or more stimulation programs, wherein the central body is configured to record data regarding the executed stimulation program and upload it to the server via the mobile device.

In some embodiments, the server is configured to provide a platform for the user to develop a customized stimulation program. In some embodiments, the data comprises stimulation parameters being used, unique identification of the central body, or a total stimulation session time. In some embodiments, custom user stimulation programs may be uploaded to the server.

In some embodiments, the server is configured to record and track the uploaded data for the user. In some embodiments, the server is configured to provide a display of the uploaded data for the user.

In some embodiments, the central body is configured to execute a plurality of different stimulation programs. In some embodiments, the plurality of different stimulation programs are user configurable at the server. In some embodiments, the plurality of different stimulation program differs in at least one of a stimulation frequency, pulse width, duty cycle parameters, ramp up and down values, burst pulse parameters, waveform shape, or interphase interval. In some embodiments, the plurality of different stimulation programs comprise a drop foot assistance program, rehabilitation program, recovery program, relaxation program, or improved performance program.

In some embodiments, the central body has a maximum dimension equal to or less than 10 cm. In some embodiments, the central body has a weight equal to or less than 30 gr. In some embodiments, the central body interfaces with the one or more pads via wired connection.

In another aspect, a method for stimulating a user is provided. The method comprises: receiving, at a mobile device, one or more stimulation programs provided by a server; receiving, at a central body, the one or more stimulation programs from the mobile device; executing, at the central body, the stimulation program; generating, at the central body, electrical pulses; transmitting the electrical pulses onto the user with aid of one or more pads to stimulate the user in accordance with the one or more stimulation programs; recording data regarding the executed stimulation program; and uploading the data to the server via the mobile device.

It shall be understood that different aspects of the invention can be appreciated individually, collectively, or in combination with each other. Various aspects of the invention described herein may be applied to any of the particular applications set forth below or for any other types of devices. Any description herein of an aerial vehicle may apply to and be used for any device, such as stimulation devices. Additionally, the systems, devices, and methods disclosed herein in the context of electrical stimulation may also be applied in the context of other types of stimulation, such as mechanical stimulation.

In some aspects, the present disclosure provides systems for providing electrical stimulation to a user. In some aspects, the system comprises one or more processors, individually or collectively, configured to communicate with one or more application programs via one or more application program interfaces (API) to obtain information on the user. In some aspects, the system comprises one or more processors, individually or collectively, configured to analyze the information on the user. In some aspects, the system comprises one or more processors, individually or collectively, configured to produce a tailored stimulation program for the user based on said analysis. In some aspects, the system comprises one or more processors, individually or collectively, configured to execute the tailored stimulation program. In some aspects, the system comprises a pulse generator configured to generate electrical pulses in response to execution of the stimulation program. In some aspects, the system comprises one or more pads in communication with the pulse generator, wherein the one or more pads are configured to be attached to the user and transmit the electrical pulses to stimulate the user. In some embodiments, the system comprises one or more processors, and the one or more processors are located on a mobile device. In some embodiments, the system comprises a mobile device, and the mobile device comprises a cell phone, tablet, or PDA. In some embodiments, the system comprises one or more processors, and the one or more processors are configured to recommend the tailored stimulation program and receive a confirmation from the user before executing the tailored stimulation program. In some aspects, the system comprises one or more processors, individually or collectively, configured to communicate with one or more application programs via one or more application program interfaces (API) to obtain information on the user, and the communication comprises an API call. In some embodiments, the API call is performed using at least one of the one or more application programs. In some embodiments, the API call is performed using a server. In some embodiments, communication between the server and the one or more application programs comprises push notifications. In some embodiments, the system comprises one or more application programs, and the one or more application programs are executable on a mobile device. In some embodiments, the system comprises one or more application programs, and the one or more application programs comprise third party programs. In some embodiments, the system comprises third party programs, and the third party programs are linked to the user. In some embodiments, the system comprises one or more APIs, and the one or more APIs comprise APIs relating to health and/or fitness. In some embodiments, the system comprises APIs relating to health and/or fitness, and the APIs relating to health and/or fitness are selected from the group consisting of Apple Health, Fitbit, Google Fit, JawBone Up, MapMyFitness, Mind Body, Moves, Nike+, RunKeeper, Strava, Under Armour Connected Fit, Wahoo Fitness, Withings, and Wodify. In some embodiments, the system comprises information on the user, and the information on the user comprises information regarding a location of the user or a change in location of the user. In some embodiments, the system comprises information on the user, and the information on the user comprises information regarding an activity of the user. In some embodiments, the system comprises an activity of the user, and the activity of the user relates to a number of steps taken by the user. In some embodiments, the system comprises an activity of the user, and the activity of the user relates to an acceleration experienced by the user. In some embodiments, the system comprises activity of the user, and the activity of the user relates to a phone usage duration by the user. In some embodiments, the system comprises an activity of the user, and the activity of the user relates to a type of activity performed by the user. In some embodiments, the system comprises a type of activity performed by the user, and the type of activity performed by the user comprises at least one selected from the group consisting of running, cycling, and weight lifting. In some embodiments, the system comprises an activity of the user, and the activity of the user relates to a number of calories consumed. In some embodiments, the system comprises an activity of the user, and the activity of the user relates to a vital sign. In some embodiments, the system comprises a vital sign, and the vital sign may be at least one selected from the group consisting of body temperature, blood pressure, heart rate, and respiratory rate. In some embodiments, the system comprises an activity of the user, and the activity of the user relates to a route taken by the user. In some embodiments, the system comprises an activity of the user, and the activity of the user relates to a workout routine performed by the user. In some embodiments, the system comprises a workout routine, and the workout routine comprises at least one selected from the group consisting of a number of repetitions and a number of sets of repetitions. In some embodiments, the system comprises information on the user, and the information on the user comprises information regarding a health of the user. In some embodiments, the system comprises information on the user, and the information regarding the health of the user comprises a health record of the user. In some embodiments, the system comprises information regarding the health of the user, and the information regarding the health of the user comprises a weight of the user. In some embodiments, the system comprises information on the user, and the user comprises information acquired by third party devices utilized by the user. In some embodiments, the system comprises a tailored stimulation program, and the tailored stimulation program is produced alongside one or more other stimulation programs. In some aspects, the system is further configured to receive from the user, a selection of the tailored stimulation program from the user prior to executing the tailored stimulation program and after producing the tailored stimulation program. In some embodiments, the system comprises a tailored stimulation program, and the tailored stimulation program is selected from a plurality of different stimulation programs. In some embodiments, the system comprises a plurality of different stimulation programs, and two or more of the plurality of different stimulation programs differ in at least one of a stimulation frequency, pulse width, duty cycle parameters, ramp up and down values, burst pulse parameters. In some embodiments, the system comprises plurality of different stimulation programs, and the plurality of different stimulation programs comprise one or more of a drop foot assistance program, rehabilitation program, recovery program, relaxation program, or improved performance program. In some embodiments, the system comprises a pulse generator, and the pulse generator interfaces with the one or more pads via wired connection. In some embodiments, the system comprises a transmission of electrical pulses to stimulate the user, and the transmission of the electrical pulses to stimulate the user improves a condition of the user.

In some aspects, the present disclosure provides methods for providing electrical stimulation to a user. In some aspects, the method comprises, with the aid of one or more processors, individually or collectively, communicating with one or more application programs via one or more application program interfaces (API) to obtain information on the user. In some aspects, the method comprises, with the aid of one or more processors, individually or collectively, analyzing the information on the user. In some aspects, the method comprises, with the aid of one or more processors, individually or collectively, producing a tailored stimulation program for the user based on said analysis. In some aspects, the method comprises, with the aid of one or more processors, individually or collectively, executing the tailored stimulation program. In some aspects, the method comprises generating, with aid a pulse generator, electrical pulses in response to execution of the stimulation program. In some aspects, the method comprises transmitting the electrical pulses with one or more pads attached to the user and in communication with the pulse generator to stimulate the user. In some embodiments, the method comprises one or more processors, and the one or more processors are located on a mobile device. In some embodiments, the method comprises a mobile device, and the mobile device comprises a cell phone, tablet, or PDA. In some embodiments, the method comprises one or more processors, and the one or more processors are configured to recommend the tailored stimulation program and receive a confirmation from the user before executing the tailored stimulation program. In some aspects, the method comprises, with the aid of one or more processors, individually or collectively, communicating with one or more application programs via one or more application program interfaces (API) to obtain information on the user, and the communication comprises an API call. In some embodiments, the API call is performed using at least one of the one or more application programs. In some embodiments, the API call is performed using a server. In some embodiments, communication between the server and the one or more application programs comprises push notifications. In some embodiments, the method comprises one or more application programs, and the one or more application programs are executable on a mobile device. In some embodiments, the method comprises one or more application programs, and the one or more application programs comprise third party programs. In some embodiments, the method comprises third party programs, and the third party programs are linked to the user. In some embodiments, the method comprises one or more APIs, and the one or more APIs comprise APIs relating to health and/or fitness. In some embodiments, the method comprises APIs relating to health and/or fitness, and the APIs relating to health and/or fitness are selected from the group consisting of Apple Health, Fitbit, Google Fit, JawBone Up, MapMyFitness, Mind Body, Moves, Nike+, RunKeeper, Strava, Under Armour Connected Fit, Wahoo Fitness, Withings, and Wodify. In some embodiments, the method comprises information on the user, and the information on the user comprises information regarding a location of the user or a change in location of the user. In some embodiments, the method comprises information on the user and the information on the user comprises information regarding an activity of the user. In some embodiments, the method comprises an activity of the user, and the activity of the user relates to a number of steps taken by the user. In some embodiments, the method comprises an activity of the user, and the activity of the user relates to an acceleration experienced by the user. In some embodiments, the method comprises an activity of the user, and the activity of the user relates to a phone usage duration by the user. In some embodiments, the method comprises an activity of the user, and the activity of the user relates to a type of activity performed by the user. In some embodiments, the method comprises a type of activity performed by the user, and the type of activity performed by the user comprises at least one selected from the group consisting of running, cycling, and weight lifting. In some embodiments, the method comprises an activity of the user, and the activity of the user relates to a number of calories consumed. In some embodiments, the method comprises an activity of the user, and the activity of the user relates to a vital sign. In some embodiments, the method comprises a vital sign, and the vital sign may be at least one selected from the group consisting of body temperature, blood pressure, heart rate, and respiratory rate. In some embodiments, the method comprises an activity of the user, and the activity of the user relates to a route taken by the user. In some embodiments, the method comprises an activity of the user, and the activity of the user relates to a workout routine performed by the user. In some embodiments, the method comprises a workout routine, and the workout routine comprises at least one selected from the group consisting of a number of repetitions, and a number of sets of repetitions. In some embodiments, the method comprises information on the user, and the information on the user comprises information regarding a health of the user. In some embodiments, the method comprises information on the user, and the information regarding the health of the user comprises a health record of the user. In some embodiments, the method comprises information regarding the health of the user, and the information regarding the health of the user comprises a weight of the user. In some embodiments, the method comprises information on the user, and the information on the user comprises information acquired by third party devices utilized by the user. In some embodiments, the method comprises a tailored stimulation program, and the tailored stimulation program is produced alongside one or more other stimulation programs. In some aspects, the method further comprises receiving from the user, a selection of the tailored stimulation program from the user prior to executing the tailored stimulation program after the tailored stimulation program for the user has been produced. In some embodiments, the method comprises a tailored stimulation program, and the tailored stimulation program is selected from a plurality of different stimulation programs. In some embodiments, the method comprises a plurality of different stimulation programs, and two or more the plurality of different stimulation program differ in at least one of a stimulation frequency, pulse width, duty cycle parameters, ramp up and down values, or burst pulse parameters. In some embodiments, the method comprises a plurality of different stimulation programs, and the plurality of different stimulation programs comprise one or more of a drop foot assistance program, rehabilitation program, recovery program, relaxation program, or improved performance program. In some embodiments, the method comprises a pulse generator, and the pulse generator interfaces with the one or more pads via wired connection. In some embodiments, the method comprises a transmission of electrical pulses to stimulate a user, and the transmission of the electrical pulses to stimulate the user improves a condition of the user.

In some aspects, the present disclosure provides electric stimulation devices for stimulating a user. In some aspects, the stimulation device comprises a central body. In some aspects, the stimulation device comprises a central body, and the central body comprises a processing unit configured to execute a stimulation program. In some aspects, the stimulation device comprises a central body, and the central body comprises a pulse generator configured to generate electrical pulses in response to the stimulation program. In some aspects, the stimulation device comprises a central body, and the central body comprises a user interface accessible on an external surface of the central body, wherein the user interface comprises an actuatable mechanism configured to affect a state of the stimulation program in two or more different ways depending on a degree of an input. In some aspects, the stimulation device comprises one or more pads in communication with the central body, wherein the one or more pads are configured to be attached to the user and transmit the electrical pulses in correspondence with the state of the stimulation program. In some embodiments, the stimulation device comprises a central body, and the central body has a maximum dimension equal to or less than 10 centimeters. In some embodiments, the stimulation device comprises a central body, and the central body has a weight equal to or less than 30 grams. In some embodiments, the stimulation device comprises a central body, and the central body interfaces with the one or more pads via wired connection. In some embodiments, the stimulation device comprises a processing unit, and the processing unit is configured to execute a plurality of different stimulation programs. In some aspects, the stimulation device comprises a mobile device. In some embodiments, the stimulation device comprises a mobile device, and the stimulation device is configured to be in communication with the mobile device. In some embodiments, the stimulation device comprises a mobile device, and the user selects the stimulation program on the mobile device. In some embodiments, the stimulation device comprises a stimulation program, and the stimulation program is uploaded from the mobile device. In some embodiments, the stimulation device comprises a user interface, and the user interface comprises a single actuatable mechanism. In some embodiments, the stimulation device comprises a single actuatable mechanism, and actuation of the single actuatable mechanism cycles between the pluralities of different stimulation programs. In some embodiments, the stimulation device comprises a plurality of different stimulation programs, and the plurality of different stimulation programs are user configurable. In some embodiments, the stimulation device comprises a plurality of different stimulation programs, and two or more of the plurality of different stimulation programs differ in at least one of a stimulation frequency, pulse width, duty cycle parameters, ramp up and down values, or burst pulse parameters. In some embodiments, the stimulation device comprises a plurality of different stimulation programs, and the plurality of different stimulation programs comprise one or more of a drop foot assistance program, rehabilitation program, recovery program, relaxation program, or improved performance program. In some embodiments, the stimulation device comprises an actuatable mechanism, and the actuatable mechanism comprises a depressible mechanism.

In some embodiments, the stimulation device comprises a depressible mechanism, and the depressible mechanism comprises a button. In some embodiments, the stimulation device comprises an actuatable mechanism, and the actuatable mechanism comprises a slidable mechanism. In some embodiments, the stimulation device comprises an actuatable mechanism, and the actuatable mechanism comprises a rotatable mechanism. In some embodiments, the stimulation device comprises an actuatable mechanism, and the actuatable mechanism is located substantially at a center of the external surface. In some embodiments, the stimulation device comprises an actuatable mechanism, and actuation of the actuatable mechanism pauses and/or resumes the stimulation program. In some embodiments, the stimulation device comprises an actuatable mechanism, and actuation of the actuatable mechanism increases and/or decreases an intensity of the stimulation program. In some embodiments, the stimulation device comprises an actuatable mechanism, and actuation of the actuatable mechanism turns on and/or turns off the electric stimulation device. In some embodiments, the stimulation device comprises an actuatable mechanism, and actuation of the actuatable mechanism is configured to affect the state of the stimulation program in four or more different ways depending on the degree of the input. In some embodiments, the stimulation device comprises four or more different ways to affect the state of the stimulation program, and the four or more different ways comprise pausing of the stimulation program, resuming of the stimulation program, increasing of an intensity of the stimulation program, and decreasing of the intensity of the stimulation program. In some embodiments, the stimulation device comprises a degree of an input, and the degree of the input is a duration of the input. In some embodiments, the stimulation device comprises a degree of an input, and the degree of the input is a force exerted for the input. In some embodiments, the stimulation device comprises a degree of an input, and the degree of the input is a direction of the input. In some embodiments, the stimulation device comprises an input, and the input comprises an actuation of the actuatable mechanism.

In some aspects, the present disclosure provides methods for stimulating a user. In some aspects, the method comprises receiving, at a central body, a stimulation program from a mobile device. In some aspects, the method comprises executing, at a processing unit of the central body, the stimulation program. In some aspects, the method comprises generating, at a pulse generator of the central body, electrical pulses in response to the stimulation program. In some aspects, the method comprises transmitting the electrical pulses at one or more pads, wherein the one or more pads are attached to the user, and wherein the one or more pads are in communication with the central body, thereby stimulating the user with the transmitted electrical pulses. In some aspects, the method comprises affecting a state of stimulation program in two or more different ways depending on a degree of an input at a user interface, wherein the user interface comprises an actuatable mechanism. In some embodiments, the method comprises a central body, and the central body has a maximum dimension equal to or less than 10 centimeters. In some embodiments, the method comprises a central body, and the central body has a weight equal to or less than 30 grams. In some embodiments, the method comprises a central body, and the central body interfaces with the one or more pads via wired connection. In some embodiments, the method comprises a processing unit, and the processing unit is configured to execute a plurality of different stimulation programs. In some aspects, the method comprises selecting the stimulation program on the mobile device by the user prior to receiving the stimulation program from the mobile device. In some embodiments, the method comprises a stimulation program, and the stimulation program is uploaded from the mobile device. In some embodiments, the method comprises a degree of an input, and the degree of the input comprises a duration of the input. In some embodiments, the method comprises a degree of an input, and the degree of the input comprises a force exerted for the input. In some embodiments, the method comprises a degree of an input, and the degree of the input comprises a direction of the input. In some embodiments, the method comprises an input, and the input comprises an actuation of the actuatable mechanism. In some embodiments, the method comprises a user interface, and the user interface comprises a single actuatable mechanism. In some embodiments, the method comprises a single actuatable mechanism, and actuation of the single actuatable mechanism cycles between the plurality of different stimulation programs. In some embodiments, the method comprises plurality of different stimulation programs, and the plurality of different stimulation programs are user configurable. In some embodiments, the method comprises a plurality of different stimulation programs, and two or more of plurality of different stimulation programs differ in at least one of a stimulation frequency, pulse width, duty cycle parameters, ramp up and down values, or burst pulse parameters. In some embodiments, the method comprises a plurality of different stimulation programs, and the plurality of different stimulation programs comprise one or more of a drop foot assistance program, rehabilitation program, recovery program, relaxation program, or improved performance program. In some embodiments, the method comprises an actuatable mechanism, and the actuatable mechanism comprises a depressible mechanism. In some embodiments, the method comprises a depressible mechanism, and the depressible mechanism comprises a button. In some embodiments, the method comprises an actuatable mechanism, and the actuatable mechanism comprises a slidable mechanism. In some embodiments, the method comprises an actuatable mechanism, and the actuatable mechanism comprises a rotatable mechanism. In some embodiments, the method comprises an actuatable mechanism, and the actuatable mechanism is located substantially at a center of the external surface. In some embodiments, the method comprises an actuatable mechanism, and actuation of the actuatable mechanism pauses and/or resumes the stimulation program. In some embodiments, the method comprises an actuatable mechanism, and actuation of the actuatable mechanism increases and/or decreases an intensity of the stimulation program. In some embodiments, the method comprises an actuatable mechanism, and actuation of the actuatable mechanism turns on and/or turns off the electric stimulation device. In some embodiments, the method comprises an actuatable mechanism, and actuation of the actuatable mechanism is configured to affect the state of the stimulation program in four or more different ways depending on the degree of the input. In some embodiments, the method comprises four or more different ways to affect the state of the stimulation, and the four or more different ways comprise pausing of the stimulation program, resuming of the stimulation program, increasing of an intensity of the stimulation program, and decreasing of the intensity of the stimulation program.

In some aspects, the present disclosure provides systems for providing electrical stimulation to a user. In some aspects, the system comprises one or more processors, individually or collectively, configured to receive an input regarding a stimulation program. In some aspects, the present disclosure provides a system for providing electrical stimulation to a user. In some aspects, the system comprises one or more processors, individually or collectively, configured to process a value of one or more stimulation parameters of the stimulation program, wherein the value is substantially randomly selected from a predefined range for the stimulation program. In some aspects, the present disclosure provides a system for providing electrical stimulation to a user. In some aspects, the system comprises one or more processors, individually or collectively, configured to execute the stimulation program. In some aspects, the system comprises a pulse generator configured to generate electrical pulses in response to execution of the stimulation program. In some aspects, the system comprises one or more pads in communication with a central body, wherein the one or more pads are configured to be attached to the user and transmit the electrical pulses, thereby stimulating the user. In some aspects, the system comprises a mobile device. In some embodiments, the system comprises a mobile phone, and the user selects a stimulation program on the mobile device. In some embodiments, the system comprises one or more stimulation parameters, and the one or more stimulation parameters are selected from the group consisting of a stimulation contraction frequency, a rest frequency, a stimulation duty cycle, a stimulation pulse width, a length of stimulation, burst pulse parameter, a ramp up time, and a ramp down time. In some embodiments, the system comprises a predefined range, and the predefined range is user configurable. In some embodiments, the system comprises a predefined range, and the predefined range is preconfigured for the stimulation program. In some embodiments, the system comprises a stimulation program, and the stimulation program comprises five or more stimulation parameters whose values are randomly selected from the predefined range for the stimulation program. In some embodiments, the system comprises five or more stimulation parameters, and a subset of the five or more stimulation parameters are randomly selected from the predefined range for the stimulation program. In some embodiments, the system comprises a subset of the five or more stimulation parameters, and the subset is randomly selected. In some embodiments, the system comprises one or more processors, and the one or more processors are configured to execute a plurality of different stimulation programs. In some embodiments, the system comprises a plurality of different stimulation programs, and the plurality of different stimulation programs are categorized into different levels. In some embodiments, the system comprises a plurality of different stimulation programs that are categorized into different levels, and the different levels comprise three or more levels. In some embodiments, the system comprises a plurality of different stimulation programs that are categorized into different levels, and the different levels determine the predefined range. In some embodiments, the system comprises a plurality of different stimulation programs, and the plurality of different stimulation programs are user configurable. In some embodiments, the system comprises a plurality of different stimulation programs, and two or more of the plurality of different stimulation program differ in at least one of a stimulation frequency, pulse width, duty cycle parameters, ramp up and down values, or burst pulse parameters. In some embodiments, the system comprises a plurality of different stimulation programs, and the plurality of different stimulation programs comprise a drop foot assistance program, rehabilitation program, recovery program, relaxation program, or improved performance program. In some embodiments, the system comprises a central body, and the central body has a maximum dimension equal to or less than 10 centimeters. In some embodiments, the system comprises a central body, and the central body has a weight equal to or less than 30 grams. In some embodiments, the system comprises a central body, and the central body interfaces with the one or more pads via wired connection.

In some aspects, the present disclosure provides methods for stimulating a user. In some aspects, the method comprises, with aid of one or more processors, individually or collectively, receiving an input regarding a stimulation program. In some aspects, the method comprises, with aid of one or more processors, individually or collectively, processing a value of one or more stimulation parameters of the stimulation program, wherein the value is substantially randomly determined from a predefined range for the stimulation program. In some aspects, the method comprises, with aid of one or more processors, individually or collectively, executing the stimulation program. In some aspects, the method comprises generating, at a pulse generator, electrical pulses in response to execution of the stimulation program, In some aspects, the method comprises transmitting the electrical pulses at one or more pads, wherein the one or more pads are configured to be attached to the user, and wherein the one or more pads are in communication with a central body, thereby stimulating the user. In some aspects, the method comprises, prior to receiving an input regarding a stimulation program, selecting the stimulation program on the mobile device by the user. In some aspects, the method comprises uploading the stimulation program from the mobile device. In some embodiments, the method comprises one or more stimulation parameters, and the one or more stimulation parameters are selected from the group consisting of a stimulation contraction frequency, a rest frequency, a stimulation duty cycle, a stimulation pulse width, a length of stimulation, burst pulse parameter, a ramp up time, and a ramp down time. In some embodiments, the method comprises a predefined range, and the predefined range is user configurable. In some embodiments, the method comprises a predefined range, and the predefined range is preconfigured for the stimulation program. In some embodiments, the method comprises a stimulation program, and the stimulation program comprises five or more stimulation parameters whose values are randomly selected from the predefined range for the stimulation program. In some embodiments, the method comprises five or more stimulation parameters, and values of a subset of the five or more stimulation parameters are randomly selected from the predefined range for the stimulation program. In some embodiments, the method comprises a subset of the five or more stimulation parameters, and the subset is randomly selected. In some embodiments, the method comprises one or more processors, and the one or more processors are configured to execute a plurality of different stimulation programs. In some embodiments, the method comprises a plurality of different stimulation programs, and the plurality of different stimulation programs are categorized into different levels. In some embodiments, the method comprises a plurality of different stimulation programs that are categorized into different levels, and the different levels comprise three or more levels. In some embodiments, the method comprises a plurality of different stimulation programs that are categorized into different levels, and the different levels determine the predefined range. In some embodiments, the method comprises a plurality of different stimulation programs, and the plurality of different stimulation programs are user configurable. In some embodiments, the method comprises a plurality of different stimulation programs, and the plurality of different stimulation programs differ in at least one of a stimulation frequency, pulse width, duty cycle parameters, ramp up and down values, burst pulse parameters. In some embodiments, the method comprises a plurality of different stimulation programs, and the plurality of different stimulation programs comprise a drop foot assistance program, rehabilitation program, recovery program, relaxation program, or improved performance program. In some embodiments, the method comprises a central body, and the central body has a maximum dimension equal to or less than 10 centimeters. In some embodiments, the method comprises a central body, and the central body has a weight equal to or less than 30 grams. In some embodiments, the method comprises a central body, and the central body interfaces with the one or more pads via wired connection.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
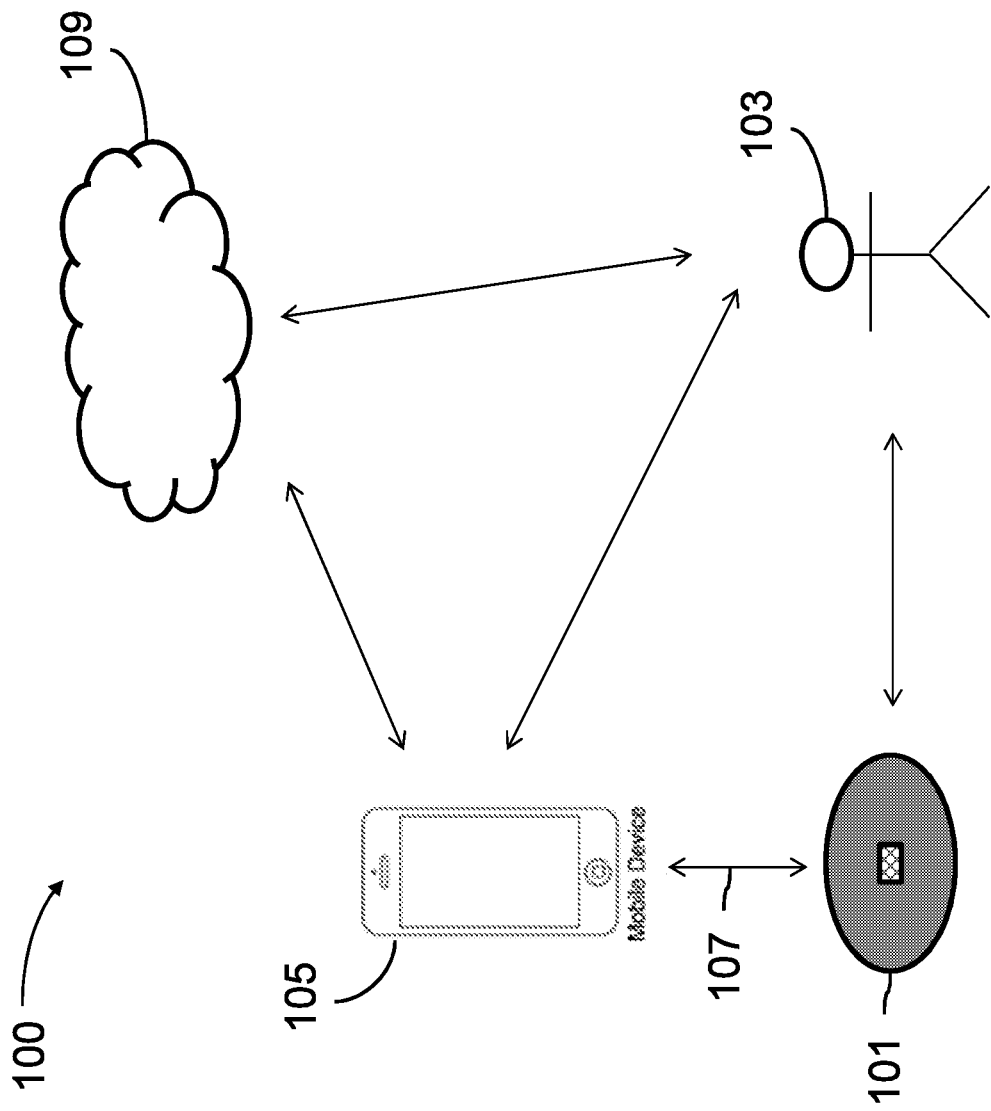
FIG. 1 illustrates a portable electrical muscular stimulation (EMS) device with a sensor system, in accordance with embodiments.

Systems, methods, and devices provided herein may provide improved functionality and usability of electrical stimulation, or electrical muscular stimulation (EMS) devices. The EMS device as described herein may be programmed, or otherwise configured to generate and/or transmit electrical impulses to a user. The EMS device may be a device programmed, or otherwise configured to implement a stimulation session, e.g. on a user. A stimulation session may refer to a session with a beginning and an end during which electrical impulses are transmitted to the user via the EMS device for the purpose of treatment, therapy, relaxation, fitness, athletic performance enhancement, entertainment, and the like. In some instances, the systems, methods, and devices of the present disclosure may help improve muscular fatigue resistance (e.g. endurance), increase muscular strength and power, improve muscular endurance and strength, improve muscle recover (e.g. through increased blood flow), and/or potentiate muscle. In some instances, a stimulation session may refer to a session with a beginning and an end implemented via a set of instructions (e.g. code, program, etc). In some instances, a stimulation session may also be referred to as a stimulation program.

As previously described herein, EMS devices may be utilized for a variety of applications. The EMS devices may be utilized for prevention of muscle atrophy. For example, the EMS device may transmit electrical impulses to muscles so as to mimic neural impulses from the brain which may stimulate muscles and prevent atrophy for patients unable to utilize certain muscles. The EMS devices may be utilized for muscle relaxation or pain reduction. For example, electrical impulses transmitted via the EMS device may counteract neural impulses that cause muscle spasms which may aid in relaxation. The EMS devices may be utilized for entertainment or general stimulation. For example, the EMS device may be utilized as a medium to deliver a stimulus in connection with modes of entertainment (e.g., virtual reality). The EMS devices may be utilized for medical purposes. For example, electrical impulses transmitted via the EMS devices may increase blood circulation which may act to prevent blood clots and/or increase healing. For example, electrical impulses transmitted via the EMS devices may aid in rehabilitation of muscles or may aid in contraction of muscles as needed (e.g., drop foot assistance). The EMS devices may be utilized for general fitness or athletic performance enhancement. For example, electrical impulses transmitted via the EMS devices may help recovery from workouts or may supplement work outs by mimicking muscle activity.

The EMS device may comprise a main body. The main body, also referred to herein as a central body, may refer to a component of the EMS device used to generate electrical impulses. For example, the central body may generate an electrical impulse by accepting a current from a battery (e.g., on board the EMS device) or from an electrical outlet. In some instances, the EMS device may further comprise one or more electrodes via which the electrical impulses may be transmitted to the user. In some instances, the EMS device may lack portability and/or ease of use. Alternatively, portable EMS devices may lack a full functionality of the larger systems or benefits that may be provided by stimulation session management by specialized technicians, healthcare professionals, or other service providers.

In some instances, the main body, also referred to herein as a central body, of the EMS device may comprise a sensor system. The sensor system may be programmed, or otherwise configured to sense signals such as signals from a muscle of a user, signals about a state of the sensor, and/or signals about an external environment. The sensor system may be utilized synergistically in conjunction with a stimulation session in order to give useful information and/or increase functionalities for the EMS device. In some instances, the integration of the sensing module on board the main body may ensure that the EMS device is simple to use and unobtrusive for the user while increasing possible applications for the EMS device.

In some instances, a plurality of EMS devices may be in communication with one another. The plurality of the EMS devices my function together as a unit in implementing a stimulation session. Alternatively or in addition, the plurality of EMS devices may implement a plurality of stimulation sessions. The plurality of EMS devices may implement stimulation sessions for a single person or a plurality of people, across different locations. In some instances, the plurality of EMS devices may be controlled by a single mobile device to implement stimulations that are varied and expansive in scope, while each EMS device remains simple to apply and unobtrusive. Data collected via the plurality of EMS devices may further be transmitted over to the mobile device for convenience of tracking and storage and may further be uploaded to a server, e.g., cloud server.

In some instances, a platform may be provided for use with the EMS devices. The platform may comprise a database, or a server where stimulation programs may be managed (e.g., created, planned, scheduled, etc). In some instances, data tracked by the EMS device and/or the mobile device may be uploaded to the platform for ease of management and monitoring. The platform may act as a central database for managing and tracking stimulation sessions. The platform may be beneficial for its users. For example, the platform may provide a convenient tool for managing and tracking stimulation sessions for the end users. For example, the platform may provide a convenient tool for specialized technicians, healthcare professionals, or other service providers to manage and track stimulation sessions for end users who may be clients.

It shall be understood that different aspects of the invention can be appreciated individually, collectively, or in combination with each other. Various aspects of the invention described herein may be applied to any of the particular applications set forth below or for any other types of stimulation devices.

FIG. 1 illustrates a system 100 for implementing a stimulation session, in accordance with embodiments. The system may utilize an EMS device 101. The EMS device may be configured to be coupled to a user 103. The EMS device may be programmed, or otherwise configured to generate electrical impulses and transmit the electrical impulses to the user. In some instances, the EMS device may implement stimulation sessions. The EMS device may comprise a central body, one or more pads, and/or other various components as further described below.

In some instances, the EMS device may be utilized in conjunction with an external device 105. For example, the EMS device may be programmed, or otherwise configured to receive signals or data from the external device 105 and/or transmit data to the external device. The external device may comprise a mobile device. Alternatively or in addition, the external device may comprise a computer (e.g., desktop computer) or any other type of device where input from a user may be accepted. While use of mobile device is primarily discussed herein, it is to be understood that any other external device may be utilized for the purpose of what is described herein with respect to mobile devices.

The mobile device may comprise cell phones, tablets, PDAs, watches (e.g. smart watches), or any other type of mobile device. The mobile device may comprise a user interface for accepting commands or instructions from a user. In some instances, the mobile device may comprise an application for controlling the central body, or EMS device. Optionally, various parameters regarding implementation of stimulation sessions may be controlled from the mobile device. The mobile device may be utilized for managing and tracking stimulation sessions. For example, a user may utilize a mobile device, or application on the mobile device, to devise (e.g., create), schedule, or plan stimulation sessions and control parameters of the stimulation sessions.

As an example, an application may be executed on the mobile device. Within the application, the user may select a desired stimulation session to be executed by the central body. In some instances, a number of predetermined stimulation sessions may be available for the user to select from. The stimulation sessions may be preloaded (e.g., contained in the application) or may be downloaded from an online database. Alternatively or additionally, the user may custom design a stimulation sessions to execute. For example, the user may design a stimulation session by varying parameters including, but not limited to, stimulation frequencies for contractions and rest periods, pulse widths, duty cycle parameters, ramp up values, ramp down values, burst pulse parameters, waveform shape, or interphase interval. The different stimulation sessions may differ in a desired effect (e.g., treatment, fitness, performance enhancement, stimulation, etc), application, and/or specific parameters (e.g., stimulation frequencies for contractions and rest periods, pulse widths, duty cycle parameters, ramp up values, ramp down values, or burst pulse parameters, etc).

As another example, stimulation sessions may be planned on the mobile device. For example, a sequence or schedule of stimulation sessions to be implemented on a user may be planned, e.g. using the mobile device. The sequence or schedule may comprise a stimulation sessions meant to be implemented on a user over time, e.g., over hours, days, weeks, months, etc.

The user may provide instructions to execute the desired (e.g., selected) stimulation session. The instructions (e.g., signals, data, etc) may be transmitted to the EMS device using wired or wireless communication 107. In some instances, the wireless communication may utilize a radio-frequency (RF) protocol. In some instances, the wireless communication may utilize an ANT+, Bluetooth Low Energy, Gazell protocol and the like. Alternatively or in addition, the user may provide instructions to stop, pause, and/or resume a stimulation session, e.g., at the mobile device. In some instances, the user may provide instructions to adjust other parameters regarding the stimulation session. For example, the user may provide instructions to adjust a stimulation intensity level of the stimulation session. The instructions may be transmitted to the central body, e.g. using the wireless communication protocol previously described herein.

Optionally, a platform may be provided for managing or tracking the stimulation sessions. In some instances, the platform may be provided on a database or a server 109, such as a cloud server. The server may be utilized for managing and tracking stimulation sessions. For example, a user may utilize the platform to devise (e.g., create), schedule, or plan stimulation sessions and control parameters of the stimulation sessions. In some instances, data tracked by the EMS devices may be uploaded to the platform, e.g., via the mobile device. The platform may provide a convenient tool for both managing and tracking stimulation sessions for the end users 103.

Figure 2:
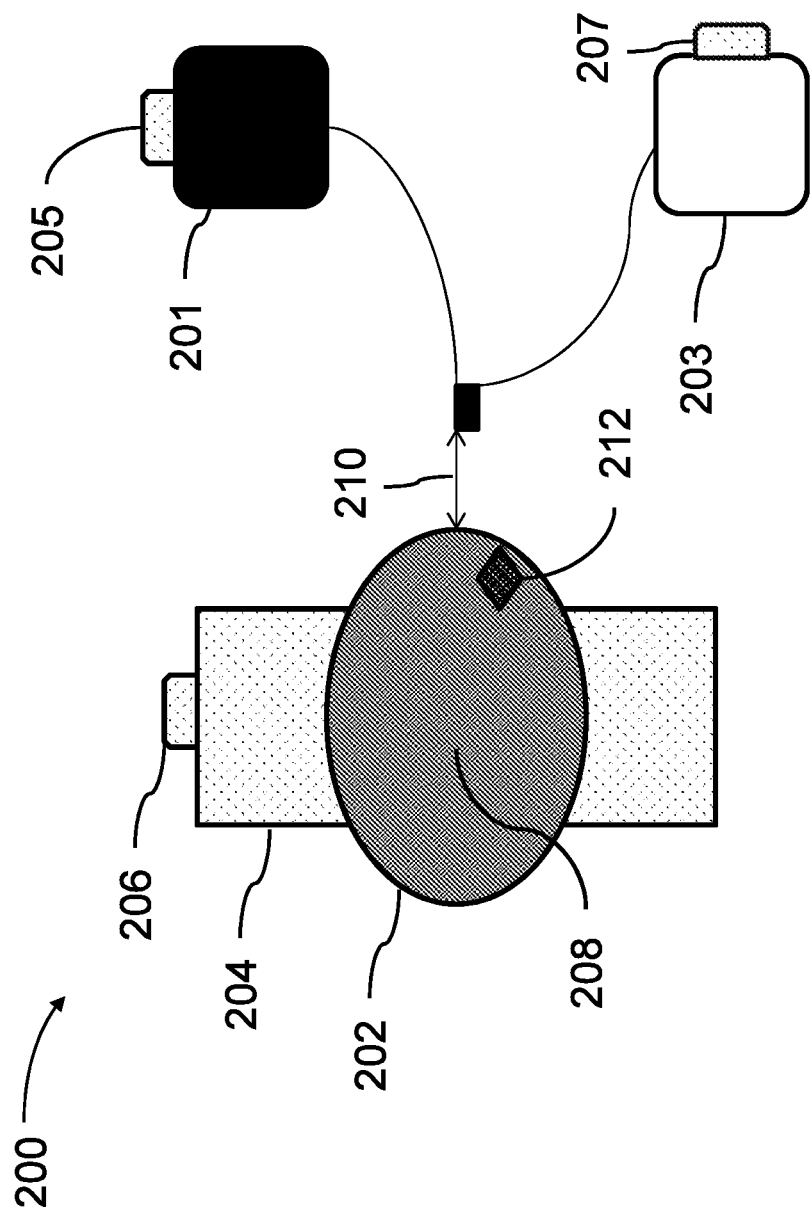
FIG. 2 illustrates an EMS device with a sensor system, in accordance with embodiments.

FIG. 2 illustrates an EMS device 200 with a sensor system, in accordance with embodiments. The EMS device 200 may be utilized in the system 100, or elsewhere throughout the application. The EMS device may comprise a central body 202. In some instances, the EMS device as described herein may refer to the central body, or the central body together with the electrodes and/or wires. The central body may be programmed, or otherwise configured to receive signals or data from the mobile device and execute and/or implement the desired stimulation session. For example, the central body may comprise a processing unit. The processing unit may be programmed, or otherwise configured to execute a stimulation program in response to the signals received. The central body may comprise a pulse generator. The pulse generator may be programmed, or otherwise configured to generate electrical impulses, e.g. in response to execution of the stimulation program. The pulse generator may be programmed, or otherwise configured to generate electrical impulses by accepting current from a battery or an electrical outlet. In some instances, the central body may comprise a battery. The battery may be a replaceable battery or an integrated battery. The battery may be rechargeable battery, such as a rechargeable lithium battery. In some instances, a port may be provided for recharging of the central body. For example, a micro-USB port may be provided as an approach for recharging the central body.

The central body may comprise stimulation channels. The stimulation channel may refer to an output channel for the generated electrical impulses. The central body may comprise any number of stimulation channels. In some instances, the central body may comprise 1, 2, 3, 4, 5, 6, 7, 8, 9, 10 or more stimulation channels. The number of stimulation channels may correspond to a number of independent output channels for the electrical impulses. For example, for each stimulation channel, a different electrical impulse may be generated and/or further transmitted by the central body. In some instances, an intensity level of all stimulation channels of the central body may be adjusted in accordance with a user's instruction, e.g. provided on the mobile device. Alternatively, an intensity level of each stimulation channel may be adjusted individually in accordance with a user's instruction.

The central body may be programmed, or otherwise configured to be in communication with one or more electrodes, or pads 201, 203. In some instances, the number of electrodes may correspond to a number of stimulation channels of the central body. Alternatively, the number of electrodes may be less than the number of stimulation channels. Alternatively, the number of electrodes may be more than the number of stimulation channels. The electrodes or pads may be configured to be applied or attached to a user. The one or more pads may comprise an adhesive. In some instances, the one or more pads may comprise tabs 205, 207 for facilitating attachment and/or removal.

The electrodes or pads may be configured to transmit the electrical impulses generated by the pulse generator to the user, thereby stimulating the user. For example, electrical impulses generated at the central body may be transmitted to the one or more pads via the connection 210, e.g. to implement a stimulation session on the user. The connection may be a wired connection. For example, the one or more pads may be physically connected to the central body via a port on the central body. The port may be a micro-USB port. In some instances, the port may be a port utilized in recharging of the battery of the central body. The utilization of the same port for recharging of the battery and for connecting with one or more electrodes may aid in miniaturization of the central body.

The central body may comprise one, two, three, four, five or more LED indicators. The LED indicator may be utilized to indicate different states of the device. For example, the central body may comprise two LED indicators. The first LED indicator may be used to indicate whether the device is turned on and/or whether the device is currently running, or executing a stimulation session. The second LED indicator may be used to indicate a battery charging status of the central body.

In some instances, the central body may be configured to be attached to, or placed on a user. For example, the central body may be attached or coupled to a user via a base unit 204. The base unit may be integrated with the central body. Alternatively, the base unit may comprise a attachable/detachable component from the central body. The base unit may be able to be attached or detached from the central body via any mechanism, e.g. snap fit mechanism, slide fit mechanism, adhesives, etc. The base unit may be reusable. Alternatively or in addition, the base unit may be configured to be replaced after a single use or a limited number of uses (e.g. appliance to the user). The base unit may comprise any unit(s) for attachment to a user. For example, the base unit may comprise an adhesive. In some instances, the adhesive may comprise one or more tabs 206 that facilitate appliance and/or removal of the EMS device. Alternatively or in addition, the base unit may comprise one or more straps.

The EMS device may be coupled to any muscle group located on the user's body. In some instances, the base unit may enable the EMS device to be coupled to any desired location on a user's body depending on a desired stimulation location and/or session. For example, the adhesive may enable the EMS device to be universally applied to any desired location on a user's body, e.g. on an arm, leg, knee, chest, abdomen, back, neck, shoulder, etc. Alternatively, the base unit may be designed for selective coupling to the user. For example, the one or more straps may be sized or shaped for selective coupling to the user's arms, abdomen, legs, neck, chest, etc.

The central body may comprise a low profile. For example, the central body may comprise a low profile such that it can be seamlessly worn under a user's clothes. The central body may comprise a height that is equal to or less than 5 cm, 4 cm, 3 cm, 2 cm, 1.5 cm, 1 cm, 0.75 cm, or 0.5 cm. The height of the central body may refer to a length of the device extending perpendicularly from the base. For example, with respect to FIG. 2, the height of the central body may extend out from the figure. In some instances, the central body may be ergonomic such that the central body may be coupled to the user (e.g., via the base unit) without interfering with everyday activities. In some instances, the central body may be ergonomic such that the central body may be coupled to the user (e.g., via the base unit) under the user's clothes and permit undertaking of normal activities. In some instances, a maximum dimension of the central body may be equal to or less than about 20 cm, 18 cm, 16 cm, 14 cm, 12 cm, 10 cm, 8 cm, 6 cm, 4 cm, or 2 cm. In some instances, a maximum volume of the central body may be equal to or less than about 500 $cm^3$, 300 $cm^3$, 100 $cm^3$, 75 $cm^3$, 50 $cm^3$, 25 $cm^3$, or 10 $cm^3$. In some instances, a weight of the central body may be equal to or less than about 100 gr, 90 gr, 80 gr, 70 gr, 60 gr, 50 gr, 40 gr, 30 gr, 20 gr, 10 gr, or 5 gr.

In some instances, the central body may comprise a simple interface 208. The simple interface may be utilized for receiving an input from a user. The simple interface may be utilized for powering on the device and powering off the device. Alternatively or in addition, the simple interface may be utilized for resetting the EMS device, pausing a stimulation session, resuming a stimulation session, and/or adjusting an intensity of the stimulation session. The simple interface may comprise buttons or switches. In some instances, the simple interface may not comprise a display that can be viewed by a user. In some instances, the simple interface may comprise at most 1, 2, 3, 4, or 5 buttons or switches. For example, the simple interface may comprise a single button interface. The single button may be utilized for powering on and powering off the EMS device as well as resetting the EMS device, pausing or resuming stimulation sessions and adjusting intensities of stimulation sessions.

In some instances, the central body may comprise a sensor system 212. The sensor system may be located anywhere on or within the central body. Alternatively or in addition, the sensor system may be located on the base unit 204. The sensor system may be programmed, or otherwise configured to sense signals from the user. In some instances, the sensor system may be programmed, or otherwise configured to record signals from a surface of a muscle, e.g. when it is contracted. The signals may comprise mechanical and/or electrical signals. For example, a mechanomyogram (MMG), or low frequency vibration may be observed and/or recorded utilizing the sensor system. The sensor system may comprise any suitable unit(s) for sensing the signals. For example, the sensor system may comprise accelerometers, gyroscopes, and/or microphones. In some instances, the accelerometer may be a 3-axis accelerometer. The sensor system may be programmed, or otherwise configured to sense signals from the user during a stimulation session.

For example, while a stimulation session is being implemented, muscles near the one or more pads may undergo contraction due to the transmitted electrical impulses. The sensor system may sense signals (e.g., vibrations) from a surface of the muscles undergoing contraction and record it for analysis. The analysis may be performed on the processing unit of the EMS device. Alternatively or in addition, sensed data may be transmitted to the mobile device, and the analysis may be performed on the mobile device. Alternatively or in addition, the analysis may be performed elsewhere. For example, the data may be transmitted to a server (e.g. cloud server) where the analysis may be performed. In some instances, processed data may be further transmitted to the mobile device and/or the server. For example, sensed data may be processed or analyzed by the processing unit which may be transmitted to the mobile device and/or the server.

In some instances, the sensor system may be programmed, or otherwise configured to sense signals from an environment, e.g. to get environmental cues. For example, an accelerometer may be programmed, or otherwise configured to record an acceleration and/or velocity with respect to a reference frame. For example, a gyroscope may be programmed, or otherwise configured to record an angular rate of rotation in a rotating reference frame. The recorded data may be utilized to analyze motions of the user. For example, based on the recorded data, a real-time gait and/or handgrip analysis may be performed. The analysis may be performed on the processing unit of the EMS device. Alternatively or in addition, sensed data may be transmitted to the mobile device, and the analysis may be performed on the mobile device. Alternatively or in addition, the analysis may be performed elsewhere. For example, the data may be transmitted to a server (e.g. cloud server) where the analysis may be performed. In some instances, processed data may be further transmitted to the mobile device and/or the server. For example, sensed data may be processed or analyzed by the processing unit which may be transmitted to the mobile device and/or the server.

The sensor system may be configured to be used in conjunction with generation of electrical impulses. In some instances, based on data read from the sensor system, the EMS device may be programmed, or otherwise configured to generate electrical impulses at appropriate times. For example, the EMS device may function as a drop foot assistance device (e.g. when coupled to a peroneal nerve and/or calf muscle) and may generate electrical impulses at appropriate times based on data sensed by the sensor system. In some instances, data may be read or sensed by the sensor system during a stimulation session in order to determine a level fatigue of the muscle under stimulation. According to MMG parameters that are sensed and/or recorded, a stimulation session may be adjusted (e.g., intensity of stimulation and/or other stimulation parameters) accordingly.

Collected data, processed or raw, may be transmitted to the mobile device. In some instances, data regarding the stimulation session that had been implemented may be recorded or tracked. For example parameters regarding the stimulation may be recorded, e.g. by the processing unit of the central body. In some instances, a stimulation length, stimulation intensity, stimulation session number, or other parameters such as stimulation frequencies for contractions and rest periods, pulse widths, duty cycle parameters, ramp up values, ramp down values, burst pulse parameters, stimulation intensity, waveform shape, or interphase interval, etc may be recorded. In some instances, data from the sensor system may be recorded or tracked. The recorded or tracked data may be configured to be transmitted to the mobile device, e.g. using a wireless communication channel.

Collected data, processed or raw, may be transmitted to a server. In some instances, collected data, processed or raw, may be transmitted to a server via the mobile device. In some instances, data regarding the stimulation session that had been implemented may be recorded or tracked. For example parameters regarding the stimulation may be recorded, e.g. by the processing unit of the central body. In some instances, a stimulation length, stimulation intensity, stimulation session number, or other parameters such as stimulation frequencies for contractions and rest periods, pulse widths, duty cycle parameters, ramp up values, ramp down values, burst pulse parameters, stimulation intensity, waveform shape, or interphase interval, etc may be recorded. In some instances, data from the sensor system may be recorded or tracked. The recorded or tracked data may be configured to be transmitted to the server, e.g. using an intermediary such as a mobile device.

The central body may be designed to minimize obtrusiveness such that it can be coupled to the user and be forgotten. As such, the aforementioned small profile, simple interface, ability to be used in conjunction with the mobile device, and/or integration of the sensor system may be of advantage. For example, the central body may be coupled to the user ergonomically and unobtrusively via adhesives or straps. The user may implement stimulation sessions via the mobile device which is used in everyday life while the small EMS device performs the stimulation unobtrusively (e.g., under the user's clothes). The user may interact with the EMS device when necessary via the simple interface. The EMS device may further provide various additional functionalities to the EMS device with an integrated sensor system without need for additional attachments such that the EMS device remains simple to use and unobtrusive. The integration of the sensor system with the central body may make sense where the central body is closely attached to a user via the base unit such that the sensor system is able to pick up, or sense, signals from the user. Data regarding the stimulation session and/or other sensed signals may be further uploaded to the mobile device and/or platform (e.g., server) for convenience of management and tracking.

Figure 3:
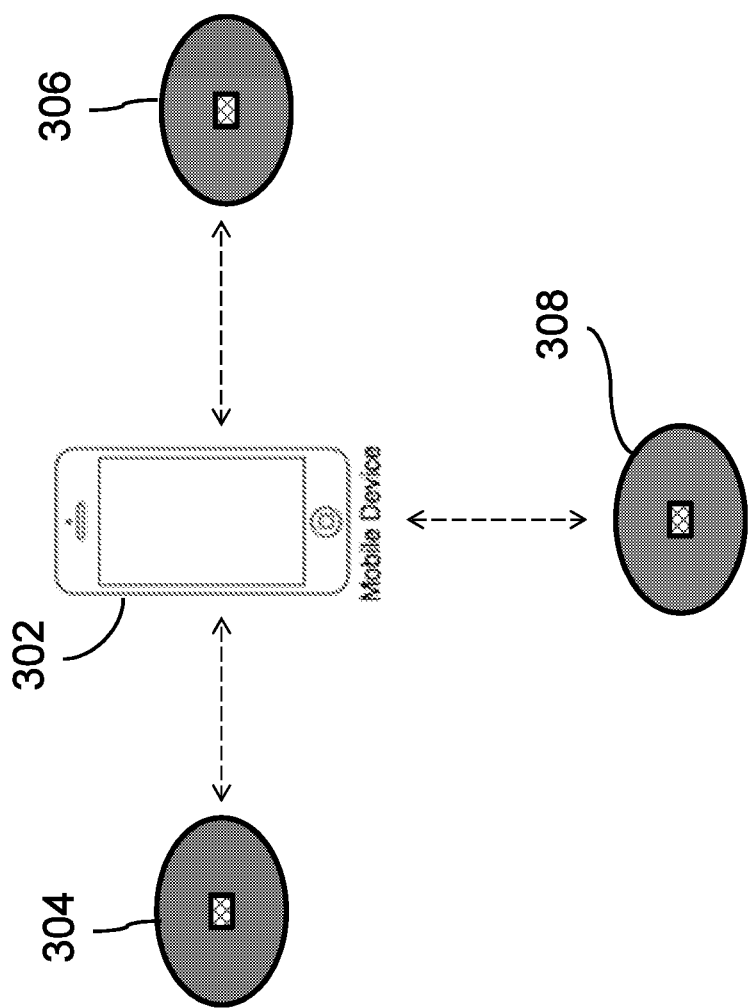
FIG. 3 illustrates a mobile device in communication with a plurality of EMS devices, in accordance with embodiments.

FIG. 3 illustrates a mobile device 302 in communication with a plurality of EMS devices 304, 306, 308, in accordance with embodiments. Each of the EMS devices may be as previously described herein. For example, each of the EMS devices may comprise a low profile, be ergonomic, comprise a simple interface, comprise a sensor system, and/or be used in conjunction with a mobile device. A single mobile device may be in communication with 1, 2, 3, 5, 7, 10, 15, 20, 50, 100, 500, 1000, 2000, 5000, 10000, 20000, 50000, 100000 or more EMS devices. The single mobile device may be in direct communication with each of the EMS devices. In some instances, the mobile device may communicate with each of the EMS devices via wireless communication by utilizing a radio-frequency (RF) protocol. In some instances, the mobile device may communicate with each of the EMS devices via wireless communication by utilizing an ANT+, Bluetooth, or Gazell protocol substantially as described herein. In some instances, the mobile device may transmit instructions for implementing a stimulation session on each of the different EMS devices 304, 306, 308. All data recorded or tracked by the EMS device (e.g. data regarding parameters of a stimulation session or data from a sensor system) may further be configured to be transmitted back to the mobile device 302.

The mobile device may be programmed, or otherwise configured to transmit a set of instructions to each of the different EMS devices. The set of instructions to be transmitted to each of the different EMS devices may or may not be different from one another. The set of instructions to be transmitted to each of the different EMS devices may be transmitted at different times, or may be transmitted simultaneously. Accordingly differing or identical stimulation sessions may be implemented via the different EMS devices at different times or simultaneously.

For example, different EMS devices may be placed on different locations of a user. The mobile device may transmit a same set of instructions to each of the different EMS devices simultaneously to implement an identical stimulation session (e.g., for fitness) on different locations on the user. In another example, different EMS devices may be placed on different users. The mobile device may transmit a same set of instructions to each of the different EMS devices to implement an identical stimulation session on different users. This may be especially applicable, for example, for healthcare professionals (e.g., doctors, therapists, nurses, etc) or other service providers (e.g., trainers) who desires to implement a same stimulation session on others simultaneously or in sequence.

In another example, different EMS devices may be placed on different parts of a user. The mobile device may transmit a different set of instructions to each of the different EMS devices to implement different stimulation sessions on different locations on the user. For example, EMS device 204 may be placed on or near a peroneal nerve of the user and provide drop foot assistance, EMS device 206 may be placed on or near a quad or hamstring muscle and provide thigh weakness rehabilitation, while EMS device 208 may be attached to a forearm of the user and assist in hand rehabilitation. In another example, different EMS device may be placed on different users. The mobile device may transmit a different set of instructions to each of the different EMS devices to implement different stimulation sessions on different users. For example, an athletic trainer may provide stimulation sessions to differing individuals that is personalized and/or targeted. This may be especially applicable, for example, for healthcare professionals (e.g., doctors, therapists, nurses, etc) or other service providers (e.g., trainers) who desires to implement different stimulation sessions on others simultaneously or in sequence.

Figure 4:
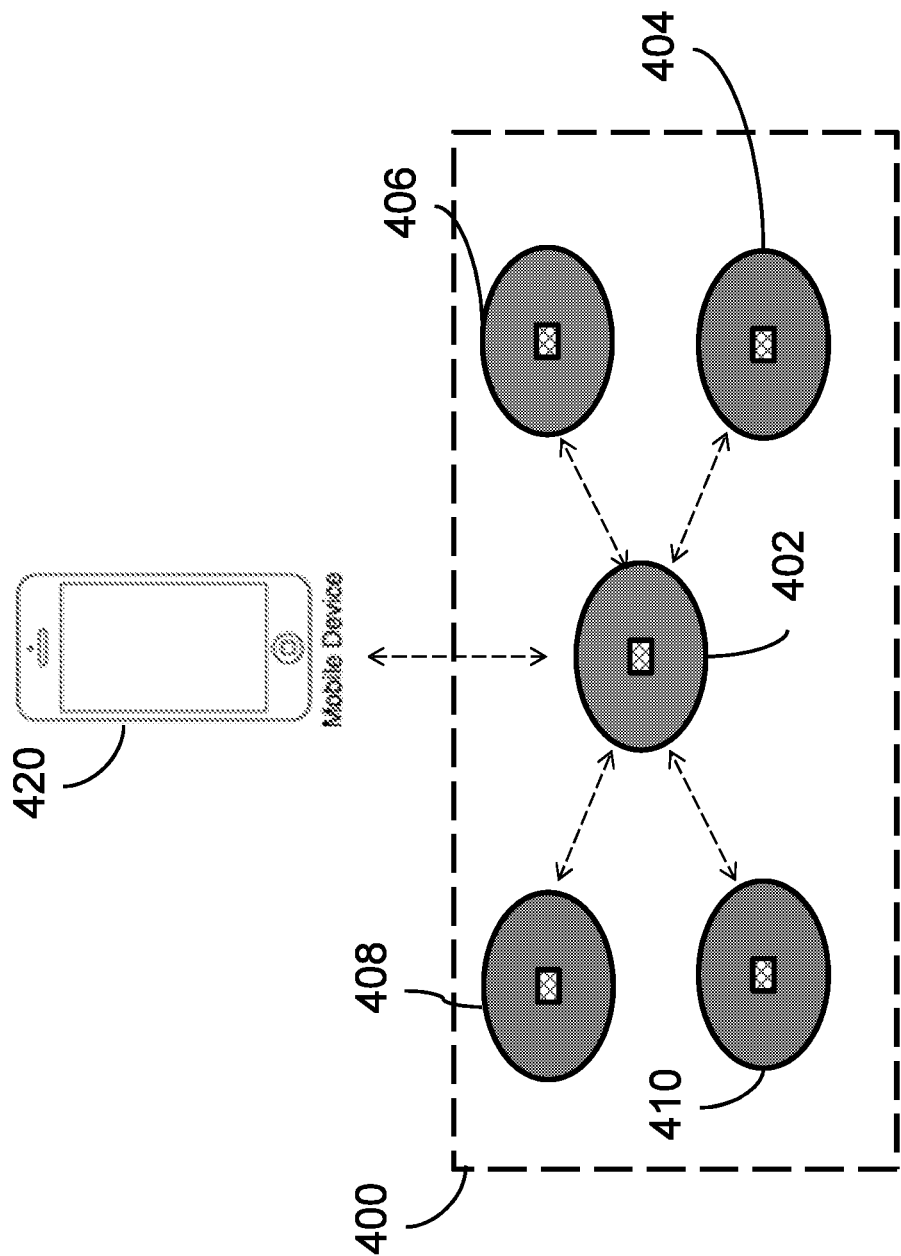
FIG. 4 illustrates an EMS device in communication with substantially similar devices, in accordance with embodiments.

In some instances, each EMS device (e.g. central body) may be programmed to, or otherwise be configured to communicate with other devices. For example, each EMS device may be programmed to, or otherwise be configured to communicate with other devices substantially similar to the EMS device. FIG. 4 illustrates an EMS device 402 in communication with substantially similar devices 404, 406, 408, 410, in accordance with embodiments. The substantially similar devices may be substantially similar in shape or size to the EMS device. For example, the similar devices may comprise a same low profile as the EMS device and may be configured to be unobtrusively coupled to a user. In some instances, the user may undertake normal daily activities while having a plurality of EMS devices on him or herself, e.g. under his clothes. Alternatively or in addition, the similar devices may comprise internal electrical components substantially similar to that of the EMS device. In some instances, the substantially similar devices may be identical to the EMS device.

The EMS device may be in communication with the other devices via wired or wireless connection. For example, the EMS device may be in communication with the other similar devices by sending and/or receiving data through a wireless communication channel. In some instances, the wireless communication channel may utilize a radio-frequency (RF) protocol. For example, the wireless communication channel may utilize an ANT+, Gazell, or Bluetooth protocols.

In some instances, the EMS device 402 together with the similar devices 404, 406, 408, 410 may comprise a set of EMS devices 400. A set of EMS devices may comprise 1, 2, 3, 4, 5, 7, 10, 15, 20, 50, 100, 500, 1000, 2000, 5000, 10000, 20000, 50000, 100000 or more EMS devices. The set of EMS devices may be programmed, or otherwise configured to implement one or more stimulation session as further described below. All data recorded or tracked by the set of EMS devices (e.g. data regarding parameters of a stimulation session or data from a sensor system) may further be configured to be transmitted back to the mobile device 420. A set of EMS devices may comprise a master device 402. In some instances, the set of EMS devices may comprise a single master device. In some instances, only the master device may be in communication with a mobile device 420.

The master device may be programmed, or otherwise configured to broadcast or distribute commands to a plurality of other similar devices 404, 406, 408, 410, e.g. via the wireless communication channel. The commands may relate to implementation and/or execution of a stimulation session. Alternatively or in addition, the master device may be programmed, or otherwise configured to receive data or signals from each of the other similar devices.

The similar devices may be programmed, or otherwise configured to receive the commands from the master device. The similar devices programmed, or otherwise configured to receive the commands from the master device may also be referred to as slave devices. The slave devices may receive the commands and implement a stimulation session. In addition, each of the slave devices may be programmed, or otherwise configured to collect and/or analyze data, substantially as described with respect to EMS devices above. The data may be data regarding the stimulation session, and/or other data sensed by a sensor system. The collected and/or analyzed data may further be transmitted to the master device. In some instance each of the slave devices may be programmed, or otherwise configured to communicate only with the master device. Alternatively, some, or all of the slave devices may be programmed, or otherwise configured to communicate with other slave devices.

The set of EMS devices may be programmed, or otherwise configured to implement one or more stimulation sessions. In some instances, the set of EMS devices may together implement a single stimulation session. For example, the master device 402 may receive a set of instructions from a mobile device 420. A processing unit of the master device may execute the set of instructions and may further transmit (e.g., broadcast) the set of instructions, or relevant parts of the instructions, to the slave devices. Each of the slave devices may further execute the received instructions. As a result the set of EMS devices may together implement a stimulation session. In some instances, all devices within the set of EMS devices may implement the stimulation session. Alternatively, a subset of the devices within the set of EMS devices may implement the stimulation session. The stimulation session may comprise differing parameters for the devices 402, 404, 406, 408, or 410. For example, although collectively implementing a stimulation session, devices 402, 404, 406, 408, or 410 may output electrical pulses that differ in parameters such as a stimulation length, stimulation intensity, stimulation session number, or other parameters such as stimulation frequencies for contractions and rest periods, pulse widths, duty cycle parameters, ramp up values, ramp down values, burst pulse parameters, stimulation intensity, waveform shape, or interphase interval.

Alternatively, the set of EMS devices implement a plurality of stimulation sessions. For example, the master device 402 may receive a set of instructions from a mobile device 420. A processing units of the master device may execute the set of instructions and may further transmit (e.g., broadcast) the set of instructions, or relevant parts of the instructions, to a subset of the slave devices. Each of the slave devices which received the instructions may further execute the received instructions to implement a stimulation session. Simultaneously or in sequence, the master device may receive a second set of instructions from the mobile device. The processing unit of the master device may execute the set of instructions and may further transmit (e.g., broadcast) the second set of instructions, or relevant parts of the instructions, to a second subset of the slave devices. Each of the slave devices which received the second set of instructions may further execute the received instructions to implement a second stimulation session. The set of EMS devices may implement 1, 2, 5, 10, 15, 20, 30, or more stimulation sessions. In some instances, the set of EMS devices may implement 1, 2, 5, 10, 15, 20, 30, or more stimulation sessions simultaneously.

Figure 5:
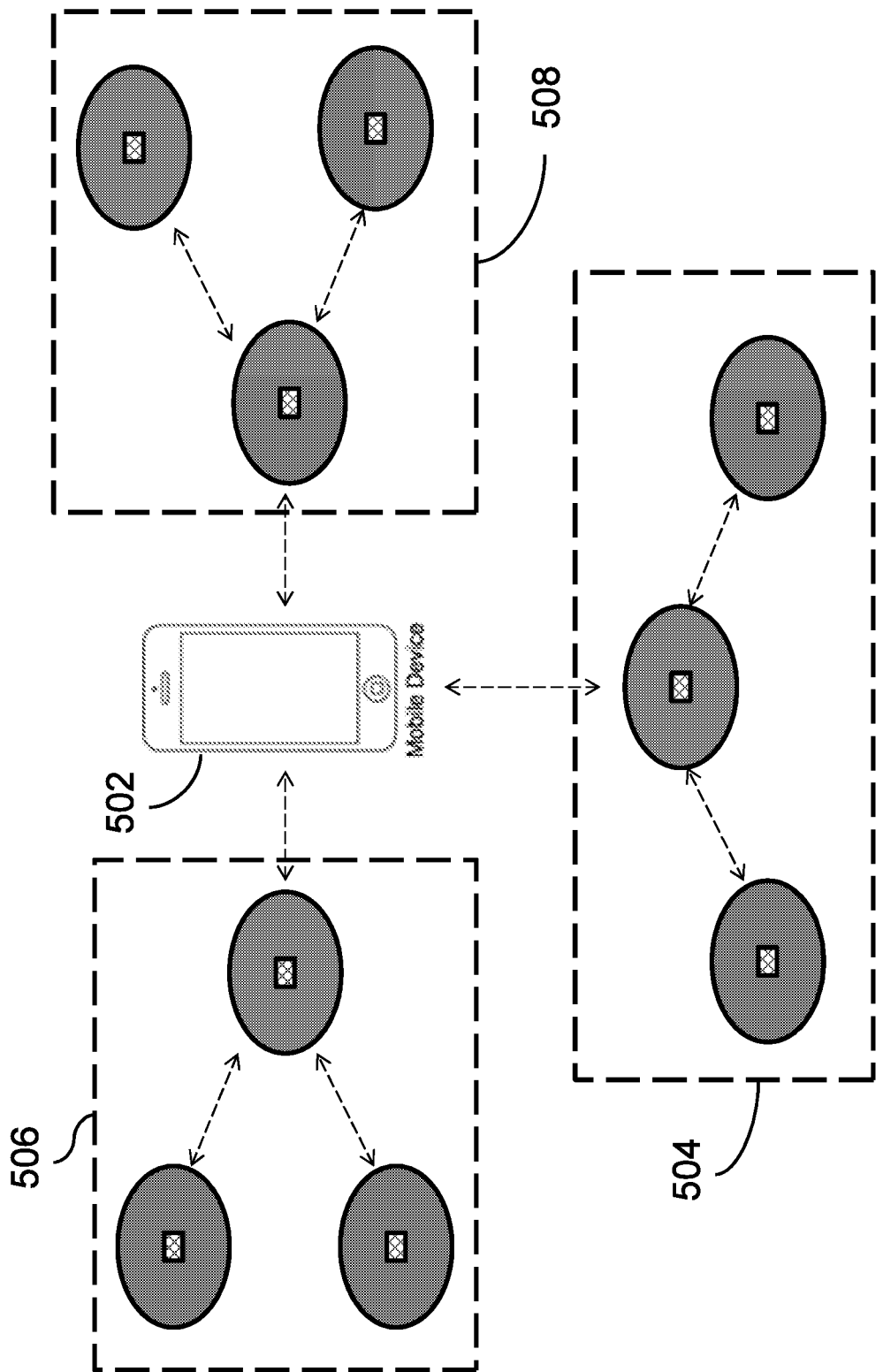
FIG. 5 illustrates a mobile device in communication with a plurality of sets of EMS devices, in accordance with embodiments.

FIG. 5 illustrates a mobile device 502 in communication with a plurality of sets of EMS devices 504, 506, 508, in accordance with embodiments. As shown in FIG. 5, a single mobile device may be coupled to a plurality of sets of EMS devices. Each set of EMS devices may be capable of implementing one or more stimulation sessions. As an example, a single mobile device may be utilized by healthcare professionals (e.g., doctors, therapists, nurses, etc) or other service providers (e.g., trainers) in implementing stimulation sessions, e.g. across different locations. For example, the first set of EMS devices 504 may be located at a first location. A service provider may provide an appropriate stimulation program(s) to an end user using his or her mobile device and collect data (e.g., data from a sensor system or data regarding stimulation session) as appropriate. Afterwards, the service provider may move to a second location with a second set of EMS devices 506. At the second location, the service provider may provide an appropriate stimulation program(s) to another end user using the same mobile device and collect data (e.g., data from a sensor system or data regarding stimulation session) as appropriate. Afterwards, the service provider may move to a third location with a third set of EMS devices 508. At the third location, the service provider may provide an appropriate stimulation program(s) to another end user using the same mobile device and collect data (e.g., data from a sensor system or data regarding stimulation session) as appropriate. Accordingly, the configuration provided in FIG. 5 may enable a service provider to utilize a single mobile device across various locations, increasing efficiency and allowing a centralized platform for capturing data regarding for his or her clients.

An ability of the EMS devices to communicate with one another or with substantially similar devices may enable each EMS device to remain small in profile and unobtrusive such that it can be integrated into everyday life while enabling the collection of EMS devices to provide stimulation sessions that are varied and expansive in scope when necessary. Moreover, the ability to manage and track stimulation sessions with a single mobile device may not only provide efficiency and convenience for end users but may provide service providers the ability to efficiently manage their clients or perform and/or demonstrate professional quality stimulations sessions to their clients who may then use the same unobtrusive EMS devices at their own convenience.

Figure 6:
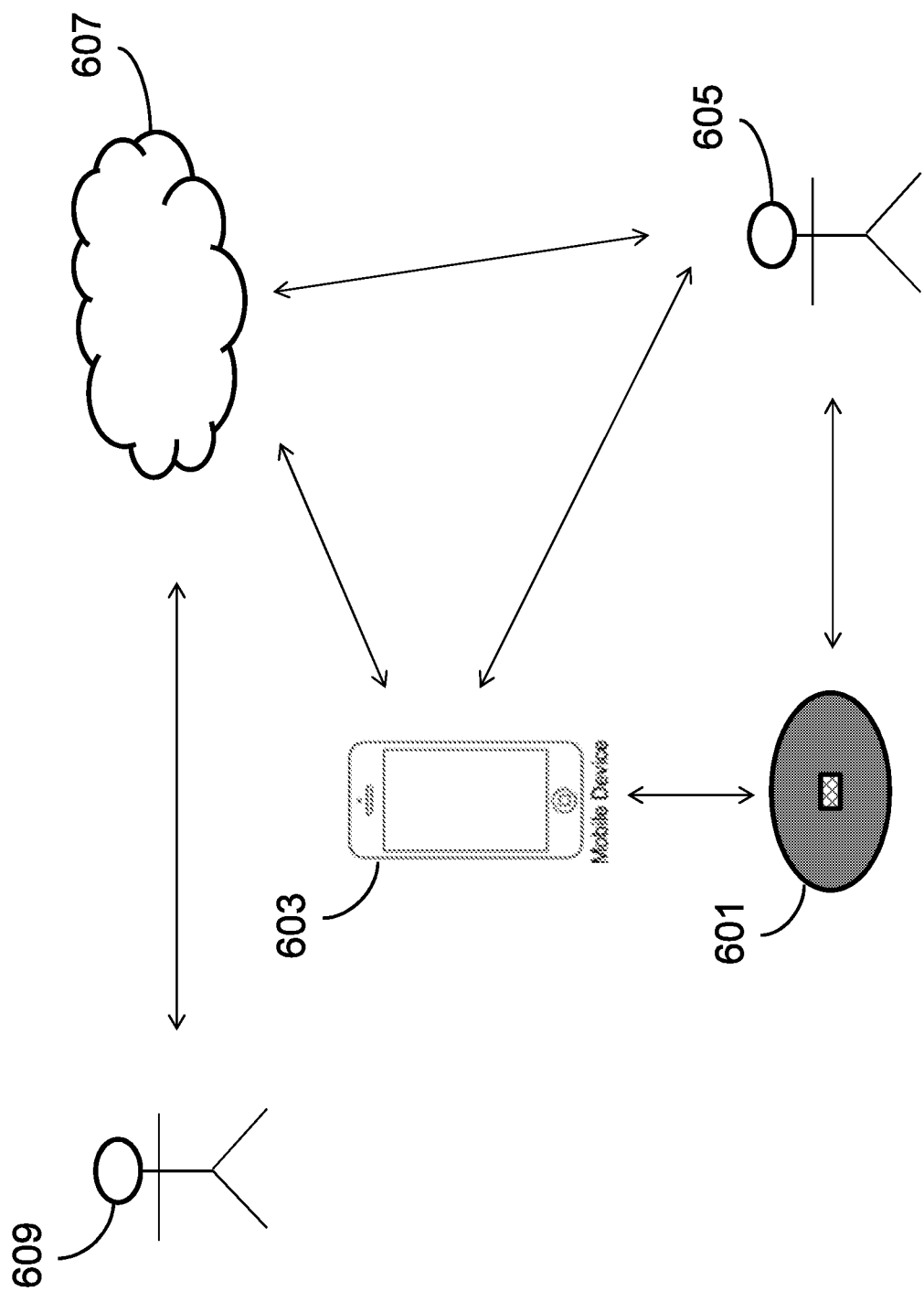
FIG. 6 illustrates a system for implementing stimulation sessions, in accordance with embodiments.

FIG. 6 illustrates a system for implementing stimulation sessions, in accordance with embodiments. Substantially as described herein, the system may comprise a plurality of components, including, but not limited to, one or more EMS devices 601, a mobile device 603, an end user 605, and/or a server 607 as described with respect to FIG. 1. In some instances, the system may additionally comprise other users 609. In some instances, the other users may be other users of an EMS device (e.g., a different EMS device from EMS device 601). In some instances, the other users may be interested individuals in EMS devices or electrical stimulation. In some instances, the other users may be a specialized technician, healthcare professional, and/or other service provider.

In some instances, the other users may create or devise a stimulation session using the platform (e.g., on the server 607), substantially as described herein. Optionally, the created stimulation session may be publicly made available for the end user 605 to download. The downloaded stimulation session may be executed and implemented, substantially as described herein using a mobile device and/or EMS device. In some instances, the publicly made available stimulation sessions may be categorized or ranked using various parameters, e.g. popularity, download number, etc. Accordingly, the platform may allow users to devise, share, and download custom designed stimulation sessions.

In some instances, the other users may create or devise planning or scheduling of various stimulation sessions. For example, the other users may plan stimulation sessions on the platform. For example, a sequence or schedule of stimulation sessions to be implemented on a user may be planned, e.g. using the platform. The sequence or schedule may comprise a stimulation sessions meant to be implemented on a user over time, e.g., over hours, days, weeks, months, etc. The scheduling and planning of the stimulation sessions may be publicly made available for the end user to download, substantially as described above.

In some instances, the platform may enable other users 609 to plan, manage, track stimulation sessions for the end user 605. In some instances, an account for an end user may be registered and/or managed by other users. Particularly, the platform may be advantageous for service providers who intend to provide customized, extensive, and/or varied stimulation sessions to a client over a period of time.

As an example, a professional user (e.g., service provider) may encounter a new end user that desires to be provided with a plan or customized stimulation sessions. The professional user may register an account for the new end user (e.g., patient account) with the platform or server 607. Alternatively or in addition, the new end user may register his or her account with the platform or server. In some instances, both the professional user and the new end user may have varying degrees of accessibility to the registered account.

The professional user may present a new stimulation session and/or associate the new stimulation session with the account of the new end user, e.g., using the platform. In some instances, the new stimulation session may be a custom designed stimulation session for the new end user. Alternatively or in addition, the new stimulation session may be a preexisting stimulation session fit for a given goal of the new end user. The professional user may additional devise and present a plan for the stimulation sessions for the new end user. For example, the professional user may associate various stimulation sessions to the registered account over time. The professional user may further track statistics regarding stimulation sessions and/or other sensor data transmitted from the user.

From the server, the stimulation plan and/or stimulation sessions may be retrieved to a mobile device 603 of the user. In some instances, the retrieval may occur automatically. Alternatively, the retrieval may occur when requested by the end user, or at set intervals. In some instances, the retrieval may be permitted only once the end user is authenticated or verified. For example, using SSL/TLS secure protocols, the end user (e.g., mobile device of the end user) may be authenticated by the server as being an appropriate personnel to retrieve the stimulation plan and/or stimulation session.

The end user 605 may apply the stimulation device 601 to his or her body. The end user may additionally utilize the mobile device and execute a relevant application for controlling the stimulation device. In some instances, the end user may select a type of stimulation session. For example, the end user may select a planned stimulation session prepared by the professional user. Alternatively or in addition, the end user may select a casual stimulation session and/or other preloaded or downloaded stimulation sessions. The end user may execute the stimulation session and/or manage progression of the stimulation sessions. In some instances, the end user may adjust an intensity of the stimulation session, e.g., using the mobile device. In some instances, the end user may configure, activate, and/or deactivate the stimulation device, e.g., using the mobile device.

The stimulation device may record data regarding the stimulation session and/or other sensed data. The stimulation device may transmit statistics or data regarding the stimulation session and/or other sensed data to the mobile application using a communication channel. The transmitted statistics or data may further be transmitted to the platform or server which may be tracked by the professional user.

Figure 7:
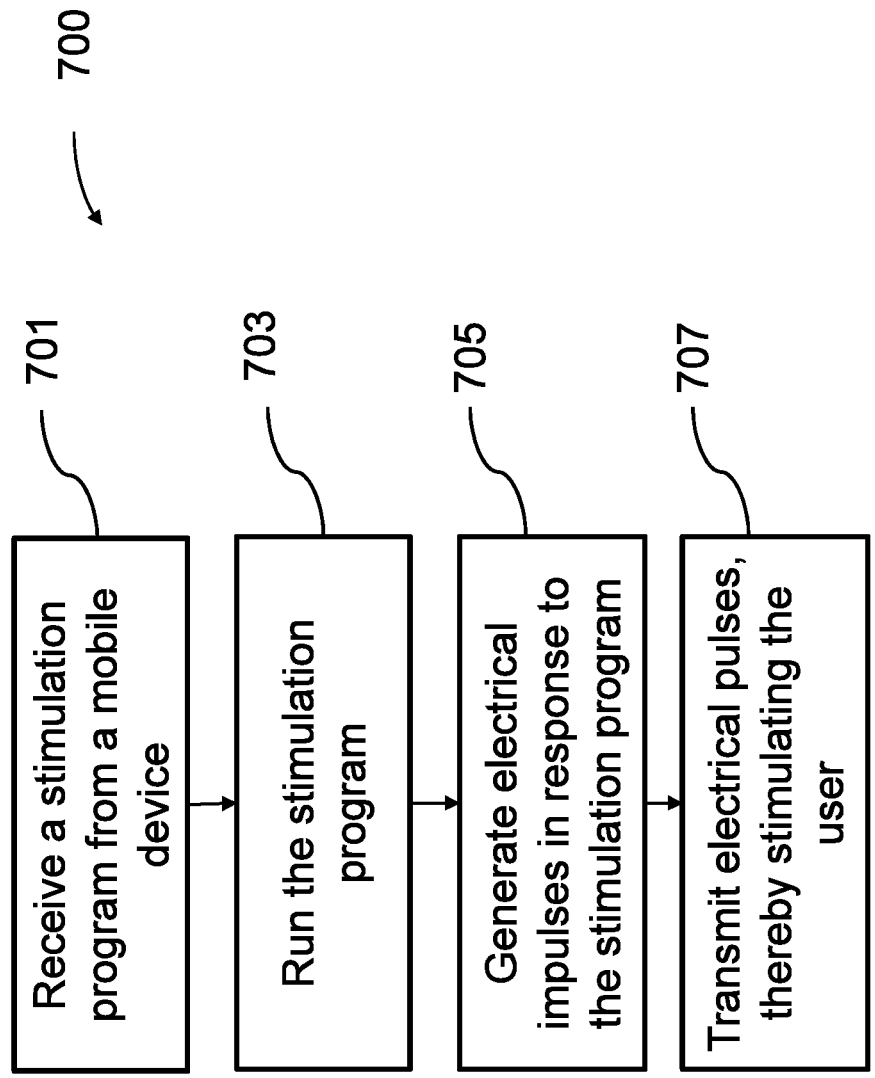
FIG. 7 illustrates a method for stimulating a user, in accordance with embodiments.

FIG. 7 illustrates a method for stimulating a user, in accordance with embodiments. Method 700 may be an example of a method in which the devices and systems described throughout may be utilized in. In step 701, a central body (e.g. of the EMS device) may receive a stimulation program from a mobile device. The central body may have a maximum dimension equal to or less than 10 cm. In some instances, the central body may have a weight equal to or less than 30 gr. The central body may comprise a sensor system programmed, or otherwise configured to sense signals, a processing unit programmed, or otherwise configured to run a stimulation program, and/or a pulse generator programmed, or otherwise configured to generate electrical impulses in response to the stimulation program, substantially as described above. In some instances, the sensor system comprises an accelerometer or a gyroscope.

In step 703, the processing unit of the central body may run, or execute the stimulation program. In some instances, the processing unit may be programmed, or otherwise configured to execute a plurality of different stimulation programs. The plurality of different stimulation programs may be user configurable. In some instances, the plurality of different stimulation programs may differ in at least one of a stimulation frequency, pulse width, duty cycle parameters, ramp up and down values, burst pulse parameters, waveform shape, or interphase interval. The plurality of different stimulation programs may be for a particular application. For example, the different stimulation programs may be to provide drop foot assistance program, for rehabilitation purposes, for recovery, for relaxation, or improved performance.

In step 705, the pulse generator of the central body may generate electrical impulses in response to the stimulation program being run. In step 707, one or more pads in communication with the central body may transmit the electrical pulses, thereby stimulating the user. The one or more pads may be configured to be attached to the user and be in communication with the central body. In some instances, the central body may interface with the one or more pads via wired connection.

In some instances, the method may further comprise sensing signals with aid of the sensor system. The sensed signals may comprise mechanomyography (MMG) readings. Alternatively or in addition, the sensed signals may comprise other EMG readings or other types of readings.

In some instances, the method may further comprise analyzing the signals sensed by the sensor system. For example, MMG readings may be analyzed to detect muscle performance parameters. For example, MMG readings may be analyzed to detect a level of muscle fatigue. In some instances, the analyzing step may relate to a gait or hand grip analysis of the user. In some instances, the processing unit of the central body may be programmed, or otherwise configured to stimulate the user and analyze the sensed signals simultaneously or sequentially.

In some instances, the method may further comprise attaching and/or removing the central body from a base unit. The attaching step may occur prior to the running of the stimulation program. The base unit may comprise different types of base units configured for attachment to different targets. In some instances, the different targets may comprise a knee, thigh, or forearm of the user. In some instances, the base unit comprises one or more straps. Alternatively or in addition, the base unit may comprise adhesives.

In some instances, an electric stimulation device for implementing the method 700 may be provided. The device may comprise: a central body comprising: a sensor system programmed, or otherwise configured to sense signals; a processing unit programmed, or otherwise configured to run a stimulation program; and a pulse generator programmed, or otherwise configured to generate electrical impulses in response to the stimulation program; and one or more pads in communication with the central body, wherein the one or more pads are configured to be attached to the user and transmit the electrical pulses, thereby stimulating the user.

In some instances, a system for implementing the method 700 may be provided. The system may comprise: a mobile device, at which the user selects a stimulation program; a central body, at which the stimulation program is received, the central body comprising: a sensor system programmed, or otherwise configured to sense signals; a processing unit programmed, or otherwise configured to run the stimulation program; and a pulse generator programmed, or otherwise configured to generate electrical impulses in response to the stimulation program; and one or more pads in communication with the central body, wherein the one or more pads are configured to be attached to the user and transmit the electrical pulses, thereby stimulating the user.

In some instances, the device for implementing the method 700, or any embodiments provided throughout may be provided in a kit. The kit may comprise any of the devices (e.g., EMS devices) described throughout and instructions for appropriately placing the device on the user. In some instances, the instructions may comprise a plurality of different appropriate placements of the device depending on a user's needs. In some instances, the plurality of different appropriate placements comprise placement of the device on a knee, thigh, or forearm of the user. For example, the instructions may explain or show the EMS device, including the central body may be placed on various parts on the user. In some instances, the instructions may explain or show how the EMS device may be universally placed on the user. In some instances, the instructions may explain or show how the EMS device may be placed under clothes of the user to allow the user to utilize the EMS device while going about his or her daily activities.

Alternatively or in addition, the kit may comprise any of the devices (e.g., EMS devices) described throughout and instructions for selecting a stimulation program and appropriately placing the device in correspondence with the stimulation program. For example, the instructions may explain utility of the device for drop foot assistance and may show and/or explain where on a user's body the device may be appropriately placed. The instruction may additionally explain the utility of the device for performing hand grip analysis and may show and/or explain where on a user's body the device may be appropriately placed. In some instances, the stimulation program may be a drop foot assistance program and the appropriate placement of the device is on or near a peroneal nerve or calf muscle of the user. In some instances, the stimulation program is a thigh rehab program and the appropriate placement of the device is on a quad or hamstring muscle of the user. In some instances, the stimulation program is a hand rehab program and the appropriate placement of the device is on a forearm of the user.

Figure 8:
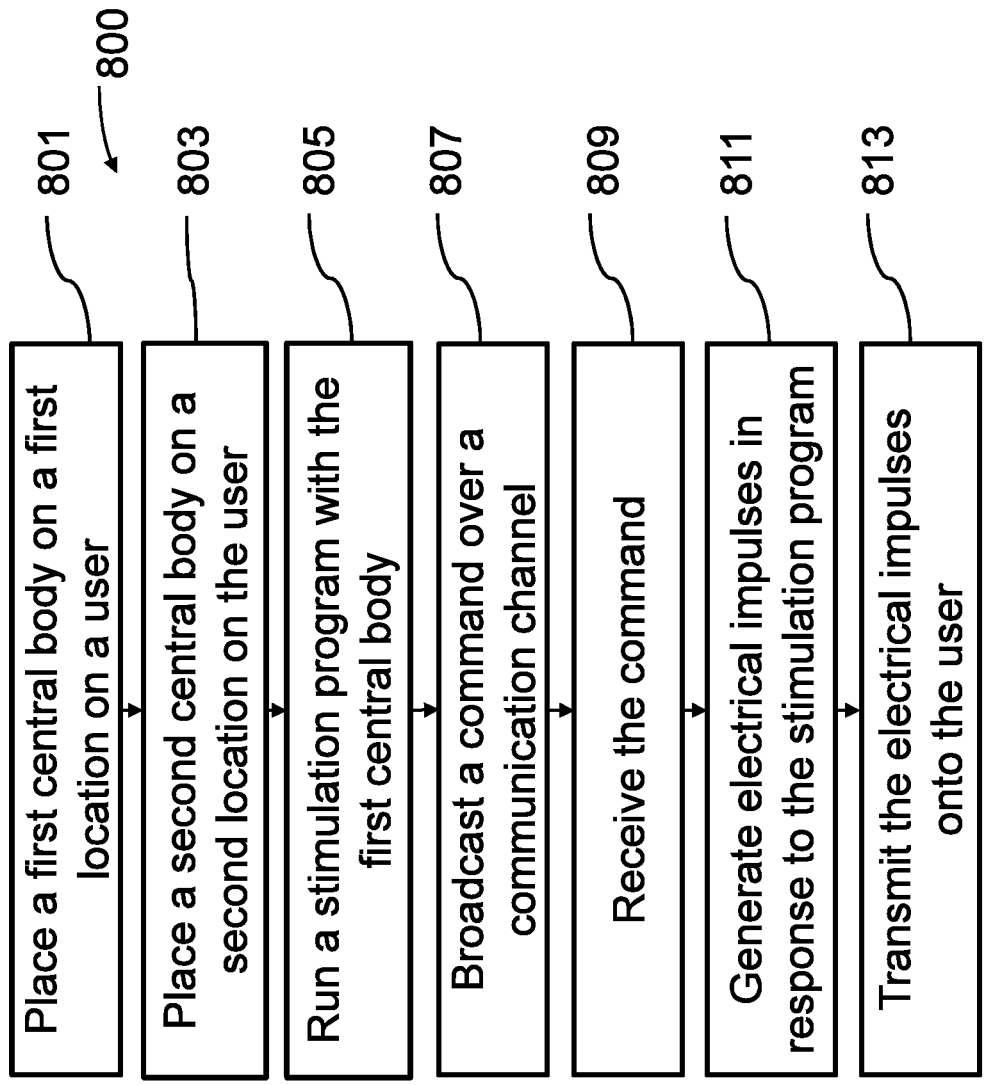
FIG. 8 illustrates a method for stimulating a user with similar devices, in accordance with embodiments.

FIG. 8 illustrates a method for stimulating a user with similar devices, in accordance with embodiments. Method 800 may be an example of a method in which the devices and systems described throughout may be utilized in. In step 801, a first central body may be placed on a first location on the user. For example, the first central body may be configured to be removably attached to a base unit which may be applied or attached to the user. For example, the base unit may comprise one or more straps and/or adhesives. The base unit may comprise different types of base units configured for attachment to different targets. In some instances, the different targets may comprise a knee, thigh, or forearm of the user. The first central body may be a central body of a device such as an EMS device, substantially as described throughout. In some instances, the first central body may have a maximum dimension equal to or less than 10 cm. Alternatively or in addition the first central body may have a weight equal to or less than 30 gr.

In step 803, a second central body may be placed on a second location of the user. For example, the second central body may be configured to be removably attached to a base unit which may be applied or attached to the user. For example, the base unit may comprise one or more straps and/or adhesives. The base unit may comprise different types of base units configured for attachment to different targets. In some instances, the different targets may comprise a knee, thigh, or forearm of the user. The second central body may be a central body of a device such as an EMS device. The second central body may be substantially similar to the first central body in some instances. In some instances, the second central body may be substantially similar in shape or size to the first central body. For example, the second central body may have a maximum dimension equal to or less than 10 cm. Alternatively or in addition the second central body may have a weight equal to or less than 30 gr. In some instances, the second central body may comprise internal electrical components substantially similar to that of the first central body.

In step 805, a stimulation program may be ran or executed with aid of a processing unit on board the first central body. In some instances, the stimulation program may be a program transmitted or uploaded from a mobile device in communication with the first central body. The mobile device may be in direct communication with the first central body. In some instances, the mobile device may be in communication with the first central body by utilizing an RF protocol such as an ANT+, Gazell, or Bluetooth Low Energy protocol. The mobile device may not be in direct communication with the second central body. Optionally, a plurality of stimulation programs may be ran or executed with aid of the processing unit on board the first central body. The plurality of stimulation programs may be ran simultaneously or in sequence. The plurality of stimulation programs may be identical, or different from one another. In some instances, the plurality of stimulation programs may be user configurable and/or user configured. In some instances, the plurality of stimulation programs may differ in at least one of a stimulation frequency, pulse width, duty cycle parameters, ramp up and down values, burst pulse parameters, waveform shape, or interphase interval from one another. In some instances, the plurality of stimulation programs may comprise programs for different purposes. For example, the programs may comprise a drop foot assistance program, rehabilitation program, recovery program, relaxation program, or improved performance program.

In step 807, a command may be broadcast over a communication channel. The broadcast may originate from the first central body. In some instances, the command may be broadcast over the communication channel as a result of running the stimulation program.

In step 809, the broadcast command may be received at the second central body. For example, a communication channel may exist between the first central body and the second central body. The communication channel may be a wireless communication channel and may utilize an RF protocol such as an ANT+ protocol, Bluetooth protocol, or Gazell protocol.

In step 811, electrical impulses may be generated in response to the stimulation program. In some instances, electrical impulses may be generated at the first central body. Alternatively or in addition, electrical impulses may be generated at the second central body. For example, the electrical impulses may be generated with aid of a pulse generator on board the first central body or the second central body.

In step 813, electrical impulses may be transmitted onto the user with one or more pads, thereby stimulating the user. In some instances, each of the central bodies may interface with one or more pads via wired connection.

In some instances, the method 800 may comprise placing a third central body on a third location on the user. Optionally, additional central bodies may be placed on different locations on the user. In some instances, a subset of the second, third, or additional central bodies may be utilized in a single stimulation program. Alternatively, all of the second, third, and additional central bodies may be utilized in a single stimulation program. In some instances, a subset or all of the second, third, and additional central bodies may be utilized in a plurality of different stimulation programs.

In some instances, an electric stimulation device for implementing method 800 may be provided. The device may comprise: a central body comprising: a processing unit programmed, or otherwise configured to run a stimulation program; and a pulse generator programmed, or otherwise configured to generate electrical impulses in response to the stimulation program, wherein the central body is programmed, or otherwise configured to 1) broadcast a command over a communication channel, and 2) communicate with one or more other bodies substantially similar to the central body, the one or more other bodies programmed, or otherwise configured to receive the broadcast command over the communication channel and generate electrical impulses in response; and one or more pads in communication with the central body or the one or more other bodies, wherein the one or more pads are configured to be attached to the user and transmit the electrical pulses, thereby stimulating the user.

In some instances, a system for implementing method 800 may be provided. The system may comprise: a first central body comprising: a processing unit programmed, or otherwise configured to run a stimulation program; and a pulse generator programmed, or otherwise configured to generate a first set of electrical impulses in response to the stimulation program, wherein the first central body is programmed, or otherwise configured to broadcast a command over a communication channel; a second central body substantially similar to the first central body, wherein the second central body is programmed, or otherwise configured to receive the broadcast command over the communication channel and generate electrical impulses in response; and one or more pads in communication with the first central body or the second central body, wherein the one or more pads are configured to be attached to the user and transmit the electrical pulses, thereby stimulating the user.

In some instances, the device for implementing the method 800, or any embodiments provided throughout may be provided in a kit. The kit may comprise any of the devices (e.g., EMS devices) described throughout and instructions for appropriately placing two or more of the device on the user. In some instances, the instructions may explain and/or visually show placing two or more of the EMS devices on a single user.

Figure 9:
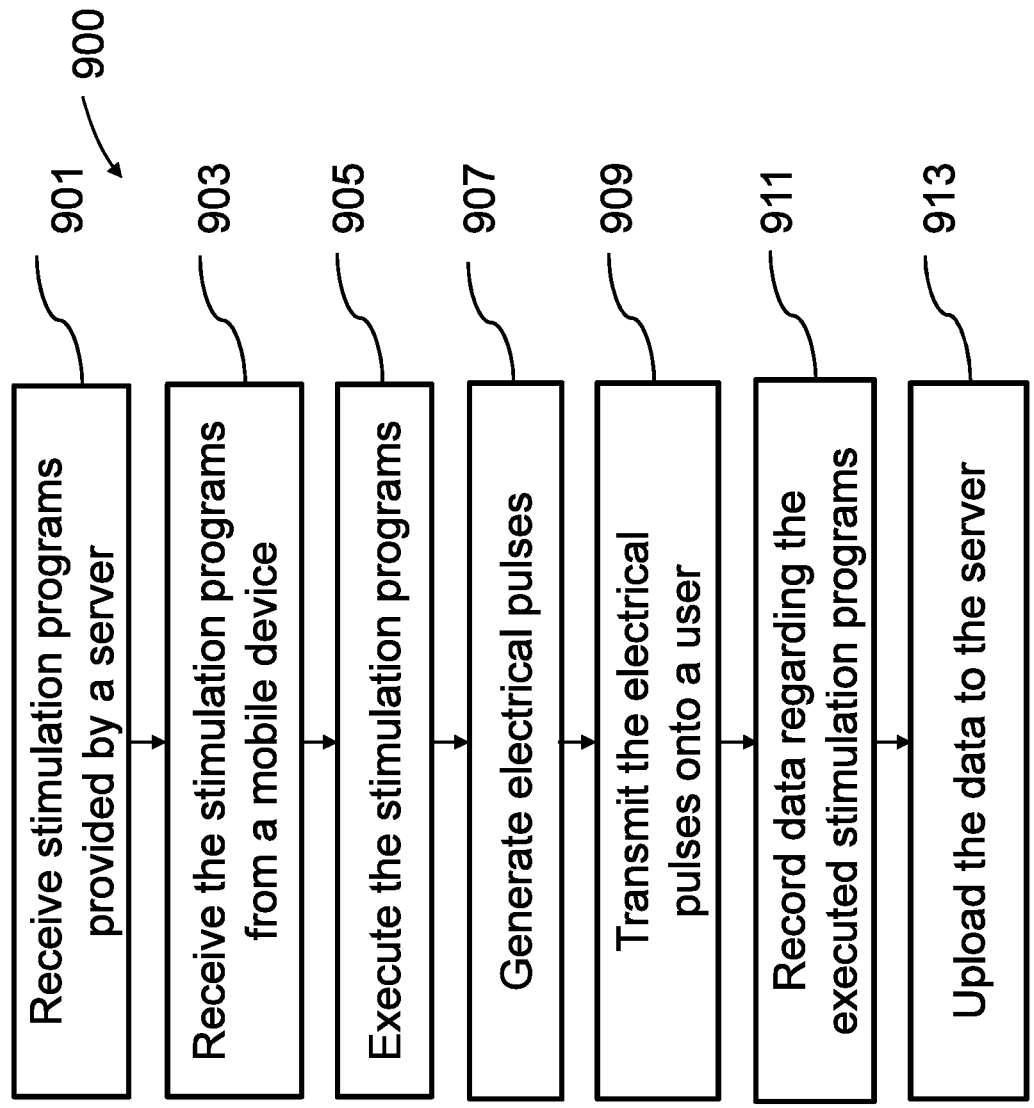
FIG. 9 illustrates a method for stimulating a user using a server, in accordance with embodiments.

FIG. 9 illustrates a method for stimulating a user using a server, in accordance with embodiments. Method 900 may be an example of a method in which the devices and systems described throughout may be utilized in. In step 901, one or more stimulation programs provided by a server may be received by a mobile device. The server may be as substantially described throughout. For example, the server may be programmed, or otherwise configured to provide a platform for the user to develop customized stimulation programs. In some instances, custom user stimulation programs may be uploaded to the server. The one or more stimulation programs provided by the server may be uploaded from users, such as a user of the EMS device. Alternatively or in addition, the one or more stimulation programs may be uploaded to the server by professional users or service providers, substantially as described throughout. Alternatively or in addition, the one or more stimulation programs may be uploaded to the server by others, such as an entity running the server.

In step 903, the one or more stimulation programs may be received at a central body. In some instances, the central body may have a maximum dimension equal to or less than 10 cm. In some instances, the central body may have a weight equal to or less than 30 gr. The one or more stimulation programs may be transmitted from the mobile device, e.g. using a communication method such as a wireless communication method. In some instances, the wireless communication method may utilize an RF protocol such as an ANT+ protocol, Bluetooth Low Energy protocol, or Gazell protocol. In some instances, any other radio-frequency protocol may be utilized.

In step 905, the stimulation program may be executed or run by the central body. For example, a firmware of the central body may execute the stimulation program. In some instances, the central body may be programmed, or otherwise configured to run a plurality of different stimulation programs. The plurality of different stimulation programs may be user configurable at the server. In some instances, the plurality of different stimulation program may differ in at least one of a stimulation frequency, pulse width, duty cycle parameters, ramp up and down values, burst pulse parameters, waveform shape, or interphase interval. In some instances, the plurality of different stimulation programs may comprise a drop foot assistance program, rehabilitation program, recovery program, relaxation program, or improved performance program.

In step 907, electrical pulses may be generated at the central body. In some instances, the electrical pulses may be generated in response to execution of the stimulation program. In step 909, the electrical pulses may be transmitted onto the user with aid of one or more pads, thereby stimulating the user. In some instances, the central body interfaces with the one or more pads via wired connection.

In step 911, data regarding the executed stimulation program may be recorded. The data may comprise information regarding stimulation parameters being used, unique IDs of the central body, or a total stimulation session time. In some instances, the data may be recorded on board a memory unit. In some instances, the memory unit may be located on board the central body. Alternatively or in addition, the data may be recorded on board a memory unit of the mobile device. In step 913, the data may be uploaded to the server via the mobile device. The server may be programmed, or otherwise configured to record and track the uploaded data for the user. In some instances, the server may be programmed, or otherwise configured to provide a display of the uploaded data for the user.

Figure 10:
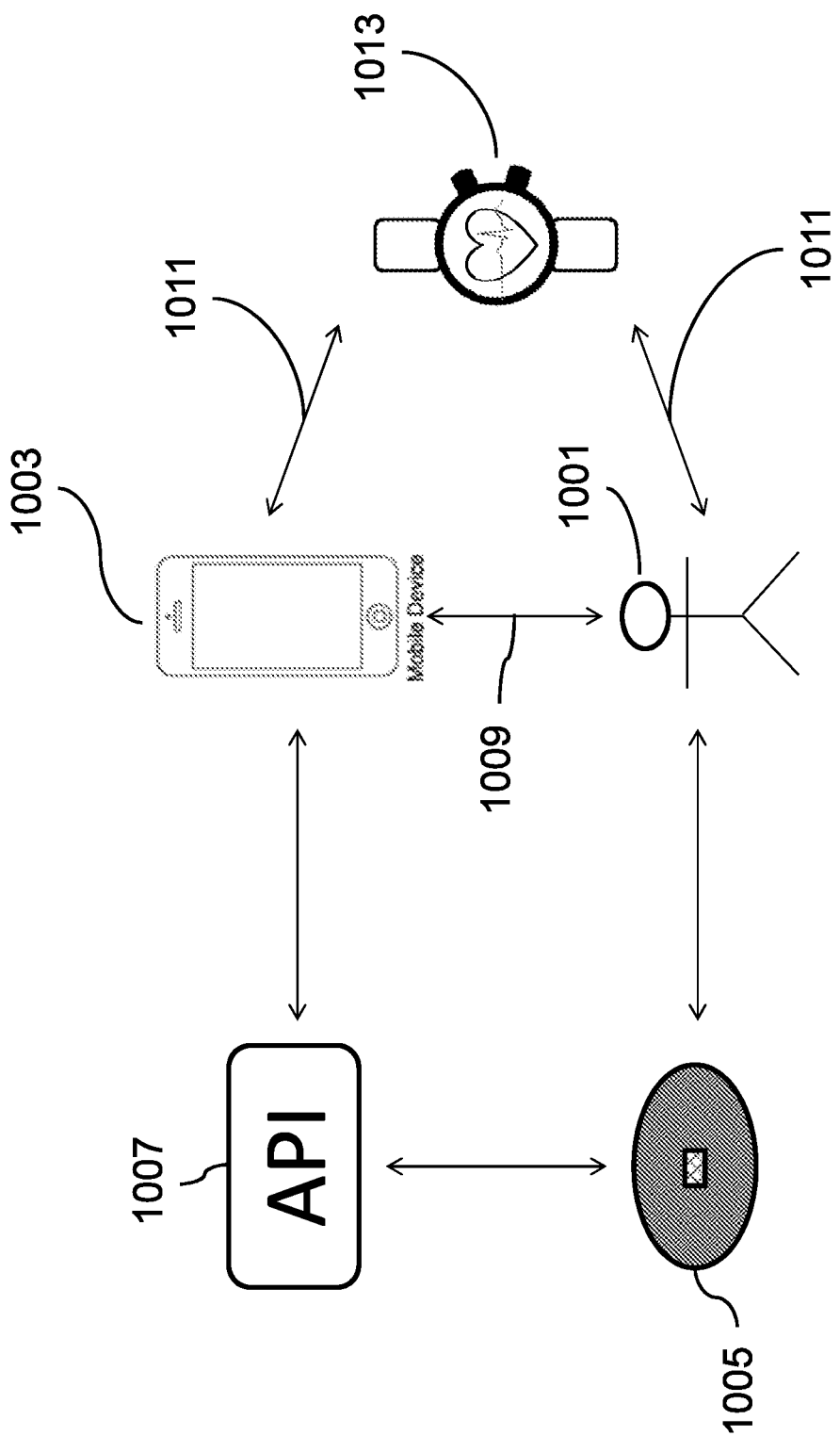
FIG. 10 illustrates a system comprising an application program interface (API) to produce a tailored stimulation program for the user, in accordance with embodiments.

FIG. 10 illustrates some embodiments of the present disclosure comprising producing and providing a tailored stimulation program to a user 1001. In some embodiments, the tailored stimulation program may be produced and executed by a system comprising one or more processors programmed, or otherwise configured to communicate with one or more application programs via one or more application program interfaces to obtain and analyze information on the user. In some embodiments, a method as disclosed herein may comprise producing and executing a tailored stimulation program with the aid of one or more processors communicating with one or more application programs to obtain and analyze information on the user.

Generally, a processor may refer to an electronic circuit that performs one or more operations on information or data from a data source. A processor may have a plurality of input/output (1/O) ports for the transmission of information into and/or out of the processor, and the I/O ports may be grouped into a plurality of ports of a specified type. In some instances, embodiments of the present disclosure may comprise one or more processors. In some instances, the embodiments of the present disclosure comprise a processing unit, and the processing unit comprises one or more processors. In some embodiments, a system, a method, and/or device as disclosed herein may comprise 1 processor. In some embodiments, a system, a method, and/or device as disclosed herein may comprise more than 1 processor. Embodiments of the present disclosure may comprise 1 processor, 2 processors, 3 processors, 4 processors, 5 processors, 6 processors, 7 processors, 8 processors, 9 processors, or 10 or more processors. Processors may be physically separate (e.g., 1 processor per chip), or combined together onto the same chip (e.g., multiple processors per chip). Some embodiments of the present disclosure may comprise 2 processors combined on a single chip (e.g., a dual-core processor). In some embodiments, 2 processors may be combined on a single chip (e.g., a dual-core processor), 3 processors may be combined on a single chip (e.g., a tri-core processor), 4 processors may be combined on a single chip (e.g., a quad-core processor), 6 processors may be combined on a single chip (e.g., a hexa-core processor), 8 processors may be combined on a single chip (e.g., an octa-core processor), and/or 10 processors may be combined on a single chip (e.g., a deca-core processor). Each of the one or more processors may operate individually or collectively. For example, a system as disclosed herein may comprise 2 processors, and the 2 processors may operate in parallel (e.g., a form of computing where calculations are subdivided into smaller tasks, assigned to at least two processors by way of a scheduler, and carried out simultaneously).

In some instances, the one or more processors may be located on mobile device 1003, such as a cell phone. Non-limiting examples of a mobile device include a cell phone, a handheld gaming console, a head mounted display, a headband, a headphone, an implantable device, an ingestible device, a mobile computer, a mobile phone, a personal digital assistant (PDA), a portable media player, a smart wristband, a smartphone, a smartwatch, and a tablet. For example, a system as disclosed herein may comprise 2 processors, and the 2 processors may be located on a cell phone. In another example, a system as disclosed herein may comprise a quad-core processor, and the quad-core processor may be located on a head-mounted display. In some embodiments, the central body 1005 of the muscle stimulation device may comprise the one or more processors.

In some embodiments, the one or more processors may be programmed, or otherwise configured to communicate with one or more application programs via one or more application program interfaces 1007 in order to obtain and analyze information on the user. In some embodiments, the application program may be running on the mobile device 1003. One category of application programs that may be useful to the embodiments of the present disclosure are health-related or fitness related applications. Health- and fitness-related application programs are commonly used to log or track information on a user (e.g., a number of steps taken). Non-limiting examples of application programs include Apple Health, Fitbit, Google Fit, JawBone Up, MapMyFitness, Mind Body, Moves, Nike+, RunKeeper, Strava, Under Armour Connected Fit, Wahoo Fitness, Withings, and Wodify. In some aspects, embodiments of the present disclosure may comprise one or more processors that are communicatively coupled with one or more application programs. A person having skill in the art will appreciate that one or more processors may be communicatively coupled to one or more application programs if there exists between them a physical (e.g., electronic circuitry) or non-physical (e.g., wireless) link such that information may be transmitted between at least one processor and at least one application program. In some instances, an application program may refer to third-party programs (e.g., a software component developed by entity other than the inventors of the present application) that may be downloaded and/or executed on a mobile phone. Communication between the one or more processors and the one or more applications may be achieved using at least one application programming interfaces (APIs) 1007. An API may generally refer to a set of routines, protocols, or tools for building software applications that may interact with a given application. In some embodiments of the present disclosure, an API may be used to access information on the user that is obtained by an application program. In some embodiments, the one or more application programs comprise third party programs, and the third party programs may be linked to the user such that the third party program is able to obtain and or receive information on the user. For example, the third party program may be linked to the motion of the user, wherein the third party program uses an accelerometer to measure a number of steps taken by the user. In another example, the third party program may be linked to a third party device (e.g., a smart watch) capable of obtaining information on the user. In yet another example, the third party program may be linked to the user, wherein the user inputs information into the third party application. A person having skill in the art will appreciate that each application program may have a unique API in order to communicate with the application program. Accordingly, any of the embodiments of the present disclosure may comprise any API necessary to communicate with a given application program in order to access, retrieve and/or obtain information on a user from the application program. For example, a system as disclosed herein may comprise one or more processors communicatively coupled with a Fitbit application program via a Fitbit API. In another example, a method may comprise, with the aid of one or more processors, communicating with a Strava application program via a Strava API. In some embodiments, an application program may be a custom program. In some embodiments, the API may me a custom application program interface. Any of the embodiments in the present application may comprise one or more processors communicatively linked to one or more custom or third party application programs via a custom API to obtain information on the user.

In any of the embodiments disclosed herein, communication between at least one application program and the API may comprise an API call. For example, communication between an application program and an API may be initiated by an API call. In some embodiments, an API call may be performed and/or initiated by the application program. In some embodiments, the API call may be performed and/or initiated by the server. In some embodiments, the server may communicate directly with the mobile application. In some embodiments, the server may communicate with the mobile application indirectly (e.g., using push notifications).

In any of the embodiments disclosed herein, information on a user may comprise information regarding the location of the user or a change in location of the user, information regarding the activity of the user, information regarding the health of the user, information acquired by third party devices utilized by the user, and/or any combination thereof. In some embodiments, information on a user may comprise information regarding a location of a user or a change in a location of the user. In some aspects, information regarding a location of a user or a change in a location of the user may be useful for identifying the position of a user, monitoring a route taken by the user, determining the distance travelled by a user, or determining the average speed of the user. For example, a system as disclosed herein may comprise two processors communicatively coupled to an application program that is programmed, or otherwise configured to monitor a route taken by the user, wherein the information comprising the route taken by the user may be transmitted between the application program and the two processors.

In some embodiments, information on a user may comprise an activity of the user. For example, an application on a mobile phone may be used to record the number of calories consumed by the user, wherein the mobile phone comprises a dual-core processor that is communicatively coupled to the application such that the information regarding calorie consumption by the user may be transmitted between the application and the dual-core processor. Non-limiting examples of an activity of a user may comprise a number of steps taken by the user, an acceleration experienced by the user, a phone usage duration by the user, a type of activity performed by the user, a number of calories consumed by the user, a vital sign of the user, a route taken by the user, a workout routine performed by the user, and/or any combination thereof. In one example, a quad-core processor may be communicatively coupled to an application that records phone usage duration by the user such that the phone usage duration by the user may be transmitted between the application and the quad-core processor. A person having skill in the art will appreciate that an activity of the user (e.g., a number of steps taken by the user, or an acceleration experienced by the user) may be determined in a variety of ways. For example, an application program may be communicatively linked to an accelerometer sensor, wherein the sensor may be used to monitor the change in the acceleration of the user and transmit the information regarding change in acceleration to the application program, wherein the application program determines if a step was taken. In another example, an application program may obtain information on the distance travelled by a user, and based on an average stepping distance approximate the number of steps taken by the user. In some embodiments, an activity of the user may comprise a type of activity of a user. In some embodiments, a type of activity of a user may comprise running. In some embodiments, a type of activity of a user may comprise walking. In some embodiments, a type of activity of a user may comprise cycling. In some embodiments, a type of activity of a user may comprise calisthenics. In some embodiments, a type of activity of a user may comprise weight lifting. It should be understood that the exemplary embodiments of types of activities provided herein are not meant to be limiting, and a person having skill in the art will appreciate that a type of activity of a user may refer to a variety actions that can be performed by a user. In some embodiments, an activity of the user may comprise a vital sign of a user. In some aspects, information comprising vital signs of the user may be useful for determining the user's overall health and providing feedback (e.g., real-time feedback) to the user information regarding their vital signs. Non-limiting examples of a vital sign of a user include body temperature, blood pressure, heart rate, respiratory rate, pulse oximetry, and any combination thereof. In some embodiments, an activity of the user may comprise a workout routine performed by a user. A workout routine may be a combination of exercises performed by a user, and/or may comprise a number of repetitions of a particular exercise and/or a number of sets of repetitions of a particular exercise. For example, a workout routine may comprise a user lifting a 30 kilogram weight 10 times (e.g., 10 repetitions) and repeating the exercise 5 times (e.g., 5 sets of 10 repetitions).

In some embodiments, information on a user may comprise information regarding the health of a user. In some embodiments, the health of a user may comprise a health record of the user. In some embodiments, the health record of the user may be provided by the user. In some embodiments, the health record of the user may comprise an electronic health record (EHR). Generally, a health record of the user may comprise information pertaining to the demographics of the user, vital signs of the user, medical history of the user, and medications taken by the user. In some embodiments, the health of a user may comprise a weight of the user. In some embodiments, the health of a user may comprise a change in weight of the user. For example, a health of the user may comprise the amount of weight lost over a period of time. In some instances, the health of a user may comprise values that are at least in part derived a weight of the user. For example, the health of a user may comprise a body mass index (BMI) of a user.

Application programs as described herein may obtain information from the user directly 1009 (e.g., the user inputs the information into the application program) or indirectly 1011 (e.g., using a third party device 1013, wherein the third party device obtains the information on a user, and the application program accesses or retrieves the information on a user from the third party device). In any of the embodiments of the present application, information on a user may comprise information acquired by a third party device utilized by the user. For example, a system as disclosed herein may comprise a smart watch, wherein the smart watch obtains information on the user and an application program is programmed, or otherwise configured to obtain or retrieve the information on the user from a smart watch. In another example, a method as disclosed herein may comprise communicating with a with an application program via an API, wherein the application program is programmed, or otherwise configured to obtain or retrieve the information on the user from a head-mounted display.

In some embodiments, one or processors may be programmed, or otherwise configured to analyze information on the user obtained from the application program, and based on the analysis produce and execute a tailored stimulation program for the user. In one embodiment, one or more processors may be programmed, or otherwise configured to analyze information on the user comprising the user's recent workout routine, and based on the analysis produce and execute a tailored stimulation program comprising the stimulation of muscles that may have been exercised in the workout routine. For example, a system as disclosed herein may comprise a quad-core processor programmed, or otherwise configured to analyze information comprising an indication that a user was recently running. Based on this information, the processor may be programmed, or otherwise configured to recommend a stimulation session comprising recovery stimulation of the calves and/or quadriceps. In another example, a method as disclosed herein may comprise analyzing information comprising an indication that a user participated in a strength training session, wherein the biceps were strained. Accordingly, the method may comprise producing, with the aid of a processor, a tailored stimulation session comprising recovery stimulation of the biceps. In yet another example, a system as disclosed herein may comprise dual-core processor programmed, or otherwise configured to analyze information comprising an indication that a user recently travelled from a first location to a second location. Based on this information, the processor may be programmed, or otherwise configured to recommend a stimulation session comprising a massage program located in the second location. In some embodiments of the present disclosure, analyzing information on the user may comprise the analysis of a single piece of information on the user (e.g., analyzing the user's location to recommend a locally available massage program). In other embodiments, analyzing information on the user may comprise the analysis of multiple pieces of information on the user (e.g., analyzing a number of steps taken by the user and an acceleration of the user to determine if the user is walking or running).

In some instances, a number of predetermined stimulation sessions may be available for the user to select from. In some embodiments of the present disclosure, the one or more processors may be programmed, or otherwise configured to produce a tailored stimulation program, based on an analysis of information on the user, alongside one or more predetermined stimulation programs that may be preloaded, downloaded from an online database, or designed by the user. In some aspects, the systems and/or methods of the present disclosure may comprise a selection by the user of a stimulation program to be executed by a processor from a plurality of stimulation programs. For example, a system as disclosed herein may comprise a processor programmed, or otherwise configured to produce a tailored stimulation program alongside a plurality of predetermined stimulation programs, wherein the user is able to select a predetermined stimulation program to be executed by the processor. In another example, a method as disclosed herein may comprise producing a tailored stimulation program alongside a plurality of predetermined stimulation programs, wherein the user is able to select the tailored stimulation program to be executed by the processor. In some embodiments, the tailored stimulation program may differ from the predetermined stimulation programs. In some embodiments, two or more of the plurality of different stimulation programs may differ in a desired effect (e.g., treatment, fitness, performance enhancement, stimulation, etc), application, and/or specific parameters (e.g., stimulation frequencies for contractions and rest periods, pulse widths, duty cycle parameters, ramp up values, ramp down values, or burst pulse parameters, etc). Furthermore, in some of the embodiments of the present disclosure, the plurality of different stimulation programs may be used, individually or in any combination, to provide drop foot assistance to the user, for rehabilitation purposes, for recovery, for relaxation, or improved performance. Any of the systems and/or methods may further comprise a pulse generator for generating electrical pulses in response to execution of the stimulation program, and one or more pads in communication with the pulse generator, and attached to the user, for transmitting electrical pulses to the user. In some embodiments of the systems and methods disclosed herein, transmission of the electrical pulses to the user may improve a condition of the user. For example, transmission of electrical pulses to the user may reduce pain. In another example transmission of electrical pulses to the user may reduce muscle fatigue.

Figure 11:
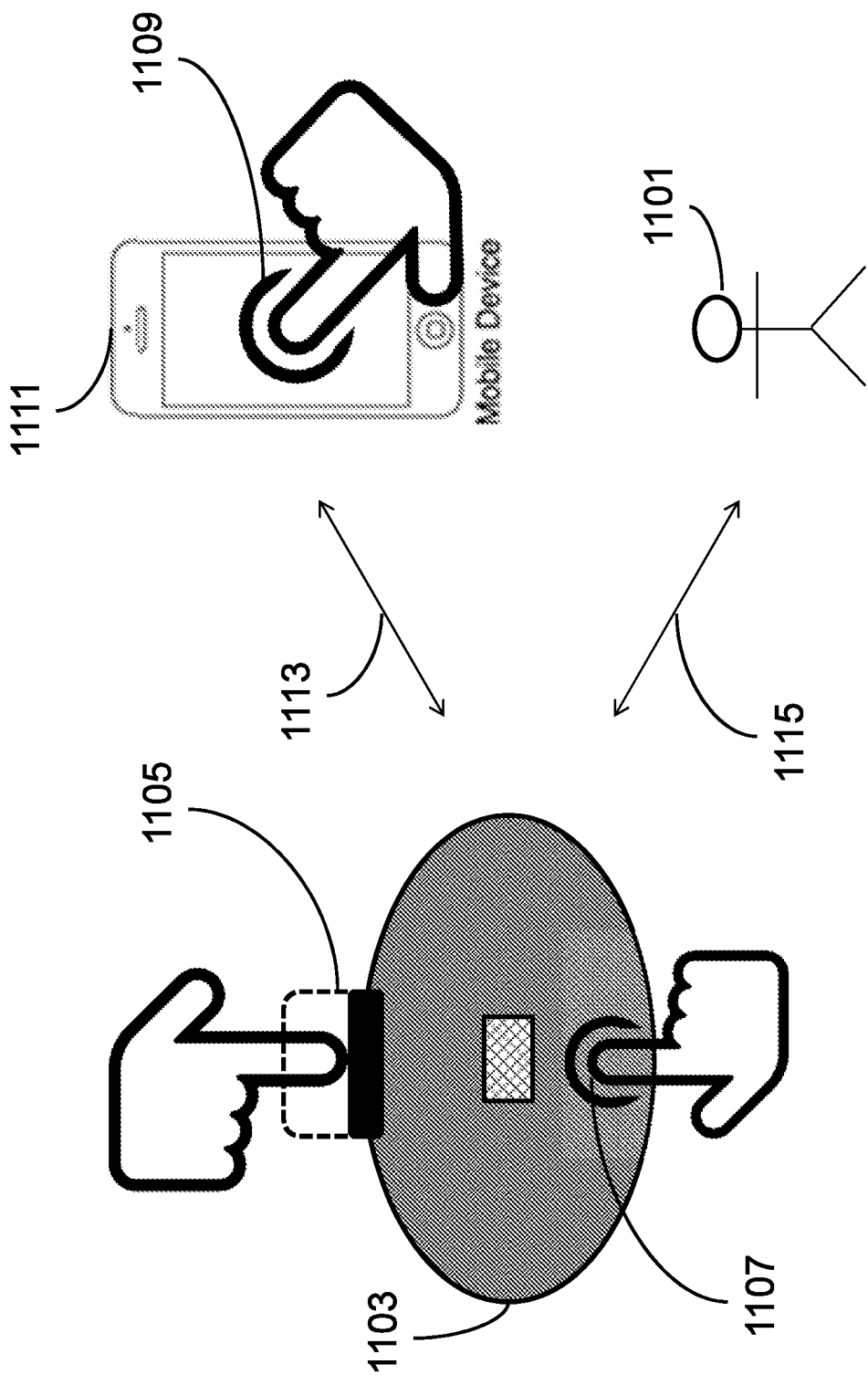
FIG. 11 illustrates a system for implementing stimulation sessions and comprising an actuatable mechanism, in accordance with embodiments.

Versatility in the actuation of an actuatable mechanism can provide a user with greater freedom to tailor a stimulation program to the user. FIG. 11 illustrates some embodiments of the present disclosure comprising devices and/or methods for stimulating a user 1101, wherein the user may, via a user interface, affect the state of stimulation in two or more different ways depending on a degree of an input. In some embodiments, an electric stimulation device as disclosed herein may comprise a user interface accessible on an external surface of a central body 1103, wherein the user interface comprises an actuatable mechanism 1105 programmed, or otherwise configured to affect a state of the stimulation program in two or more different ways depending on a degree of an input. In some embodiments, the device may further comprise one or more pads in communication with the central body, wherein the one or more pads are configured to be attached to the user and transmit the electrical pulses in correspondence with the state of the stimulation program. In some embodiments, a method for stimulating a user as disclosed herein may comprise affecting a state of stimulation program in two or more different ways depending on a degree of an input at a user interface, wherein the user interface comprises an actuatable mechanism.

In some embodiments, a device or method as disclosed herein may comprise at least one actuatable mechanism capable of, upon actuation, affecting the state of a stimulation program. In some aspects, embodiments of the present disclosure may comprise 1 actuatable mechanism. In some aspects, embodiments of the present disclosure may comprise 2 actuatable mechanisms, 3 actuatable mechanisms, 4 actuatable mechanisms, or 5 or more actuatable mechanisms. For example, an electrical stimulation device as disclosed herein may comprise 1 actuatable mechanism.

In some embodiments, the actuatable mechanism may be a depressible mechanism 1105, such as button or microswitch. In other embodiments, the actuatable mechanism may be a slidable or rotatable mechanism. In some embodiments comprising two or more actuatable mechanisms, each actuatable mechanism may be separately selected from the group consisting of depressible mechanisms, slidable mechanisms, and rotatable mechanisms. In some embodiments, the mechanism may be a physical mechanism. In some embodiments, the actuatable mechanism may be touch-sensitive 1107. In some embodiments, the mechanism may be a touch-sensitive virtual mechanism 1109 (e.g., a virtual button). In some embodiments, the virtual mechanism may be virtually depressible, virtually slidable, or virtually rotatable, thereby giving the illusion of a physical actuatable mechanism. For example, some embodiments of the present disclosure may comprise a mobile device 1111 communicatively coupled with a connection 1113 to an electrical stimulation device, wherein depression of the actuatable mechanism virtually coded in the mobile phone transmits a signal from the mobile device to the electrical stimulation device thereby affecting the stimulation program. In some embodiments, the connection 1113 may comprise a one-way or two-way wired or wireless connection, such as a WiFi connection, a Bluetooth connect, a Bluetooth LE, an ANT+ connection, or a Gazell connection. In some embodiments, the central body 1103 may be attached, adhered, or otherwise coupled to the user 1101 through touching contact 1115.

A person having skill in the art will appreciate that one or more actuatable mechanisms may be located anywhere on the external surface of an electrical stimulation device. In some embodiments, an actuatable mechanism may be located on the front face of a central body of the electrical stimulation device. In some embodiments, an actuatable mechanism may be located on the left side of a central body of the electrical stimulation device. In some embodiments, an actuatable mechanism may be located on the right side of a central body of the electrical stimulation device. In some embodiments, an actuatable mechanism may be located on the left side of a central body of the electrical stimulation device. In some embodiments, an actuatable mechanism may be located on the top side of a central body of the electrical stimulation device. In some embodiments, an actuatable mechanism may be located on the bottom side of a central body of the electrical stimulation device. In some embodiments, an actuatable mechanism may be located substantially at the center of an external surface of the electrical stimulation device.

In some embodiments, actuation of the one or more actuatable mechanisms may permit the user to cycle between a plurality of different stimulation programs. For example, actuation of the actuatable mechanism may cause an electrical stimulation device to switch from executing a first stimulation program to a second stimulation program. In another example, actuation of the actuatable mechanism may cause an electrical stimulation device to switch from an off state to executing a first stimulation program. In the same example, actuation of the actuatable mechanism a second time may cause the electrical stimulation device to switch from executing a first stimulation program to an off state. It should appreciated that an off state in any of the embodiments disclosed herein may refer to an idle state (e.g., wherein the device may be on but the stimulation program is paused) or a powered down state (e.g., wherein the electrical stimulation device is powered off. In some embodiments, actuation of the actuatable mechanism may affect the intensity of the stimulation program. For example, an electrical stimulation device as disclosed herein may comprise a depressible mechanism, and actuation of the depressible mechanism may cause the pulse width to increase. In another example, an electrical stimulation device as disclosed herein may comprise a rotatable mechanism, and rotation of the rotatable mechanism may cause the stimulation frequency to increase. Any of the embodiments of the present invention may comprise more than on actuatable mechanism, and the actuation of two or more actuatable mechanisms may be required to affect the stimulation program.

In some embodiments, the degree of an input may affect the state of the stimulation program. Non-limiting examples of a degree of an input that may be varied include the number of inputs (e.g., number of times an actuatable mechanism is actuated and released in succession), the speed of an input (e.g., the speed at which an actuatable mechanism is actuated and/or released), the duration of an input (e.g., the amount of time that an actuatable mechanism is actuated), the force exerted for the input (e.g., the force with which an actuatable mechanism is actuated), or the direction of an input. In an of the embodiments as disclosed herein, an input may comprise actuation of an actuatable mechanism. In one example, an electrical stimulation device may comprise a depressible mechanism, and briefly (e.g., less than half of one second) depressing and releasing the depressible mechanism may pause the current stimulation session. In another example, a paused stimulation session may be resumed by depressing a depressible mechanism for 1-2 seconds. In yet another example, an electrical stimulation device may comprise a depressible mechanism, and depression of the depressible mechanism for greater than 2 seconds may increase the intensity of the current stimulation session. In some embodiments, actuation of the actuatable mechanism may be programmed, or otherwise configured to affect the state of the stimulation program in one way. In some embodiments, actuation of the actuatable mechanism may be programmed, or otherwise configured to affect the state of the stimulation program in more than one way, depending on the degree of the input. In some embodiments, actuation of the actuatable mechanism may be programmed, or otherwise configured to affect the state of the stimulation program in 2 ways, 3 ways, 4 ways, 5 ways, 6 ways, 7 ways, 8 ways, 9 ways, or 10 or more ways, depending on the degree of the input. In one example comprising an actuatable mechanism programmed, or otherwise configured to affect the state of the stimulation program in 2 ways, an electrical stimulation device may comprise a depressible mechanism, and briefly (e.g., less than half of one second) depressing and releasing the depressible mechanism may increase the intensity of the current stimulation session by one level, whereas depressing a depressible mechanism for 1-2 seconds may decrease the intensity of the current stimulation session by one level. A person having skill in the art will appreciate that the state of the stimulation program may be affected in a variety of ways. Non-limiting examples of ways in which the state of a stimulation program may be affected include pausing of the stimulation program, turning off the stimulation switching to a different stimulation program, resuming of the stimulation program, increasing of an intensity of the stimulation program, and decreasing of the intensity of the stimulation program. In one example, an actuatable mechanism may be programmed, or otherwise configured to affect the state of the stimulation in 4 or more different ways, wherein the 4 or more different ways comprise pausing of the stimulation program, resuming of the stimulation program, increasing of an intensity of the stimulation program, and decreasing of the intensity of the stimulation program.

Figure 12:
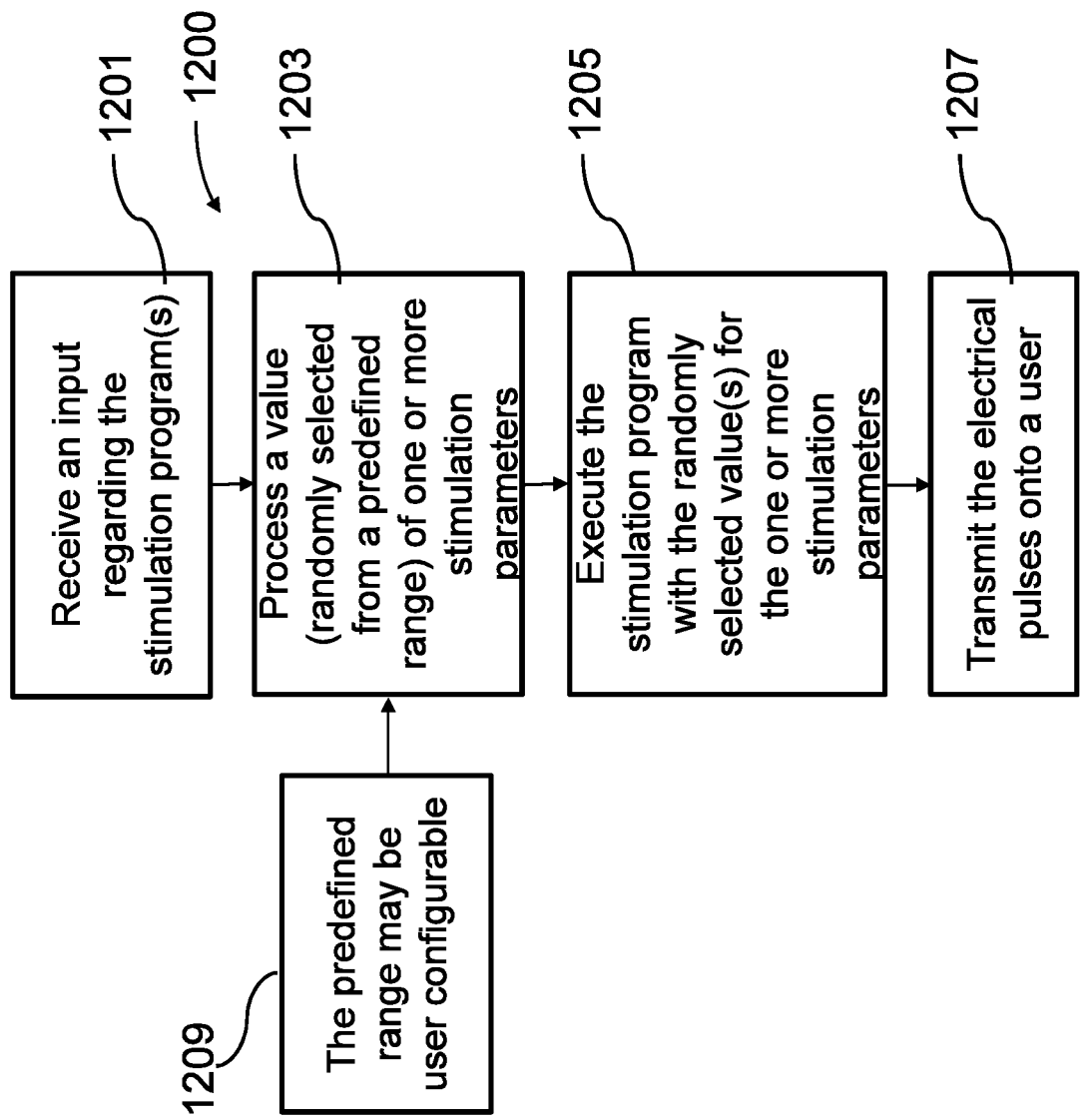
FIG. 12 illustrates a method for stimulating a user using randomly selected values for one or more stimulation parameters, in accordance with embodiments.

Random modification of at least one stimulation parameter between successive stimulation runs, stimulation program phases or levels can prevent muscle adaption to the same electrical stimulation modalities, and thereby improve the efficiency of the stimulation. For example, random modification of at least one stimulation parameter may improve fatigue resistance (e.g., endurance). In another example, random modification of at least one stimulation parameter may increase force production. FIG. 12 illustrates some embodiments of the present disclosure comprising a method 1200 for stimulating a user comprising a plurality of steps, wherein each step may comprise one or more sub-steps. One or more steps or sub-steps of the method 1200 may be repeated, omitted, or performed in a different sequence as described herein as appropriate to stimulate the user as desired. In a step 1201, an input regarding one or more stimulation programs may be received by any component of a device or a system as disclosed herein (e.g., an EMS device, a central body, a processor, or a mobile device). In a step 1203, a value of the one or more stimulation parameters may be processed. The processed stimulation parameter may be randomly selected from a predefined range as described herein. In a step 1205, the stimulation program may be executed with the randomly selected values for the one or more stimulation parameters. In a step 1207, the electrical pulses may be transmitted onto a user. In a step 1209, the predefined range, from which a value of the one or more stimulation parameters may be selected, may be user configurable. Any of the stimulation parameters in the present disclosure may be randomized within a predefined range. Non-limiting examples of parameters that may be randomized include stimulation contraction frequency, rest frequency, stimulation duty cycle, stimulation pulse width, length or duration of stimulation, burst pulse parameter, ramp up time, ramp down time, or any combination thereof. In one example the contraction frequency may be randomly selected from a value between 80 and 100 Hz. In some embodiments, a single stimulation parameter may be randomized. In some embodiments, 2 stimulation parameters, 3 stimulation parameters, 4 stimulation parameters, 5 stimulation parameters, 6 stimulation parameters, 7 stimulation parameters, 8 stimulation parameters, 9 stimulation parameters, or 10 or more stimulation parameters may be randomized, each within a uniquely defined range for a particular stimulation program. In some embodiments, a subset of 2 stimulation parameters, a subset of 3 stimulation parameters, a subset of 4 stimulation parameters, a subset of 5 stimulation parameters, a subset of 6 stimulation parameters, a subset of 7 stimulation parameters, a subset of 8 stimulation parameters, a subset of 9 stimulation parameters, or a subset of 10 or more stimulation parameters may be randomized, each within a uniquely defined range for a particular stimulation program. In some embodiments, two or more of the plurality of different stimulation programs may differ in a desired effect (e.g., treatment, fitness, performance enhancement, stimulation, etc). Accordingly, the predefined range for a given stimulation parameter may be different for different stimulation programs. In some embodiments, the predefined ranges may be user configurable 1209. In some embodiments, the predefined ranges may be preconfigured for a particular stimulation program. In one example, stimulation parameters of one phase of a Strength electrical muscle stimulation program may be varied within the following ranges: contraction frequency: 80-100 hertz (Hz), rest frequency: 0-5 Hz, contraction time: 3-5 seconds, rest time: 15-30 seconds, pulse width: 200-400 uS, length of stimulation: 20-50 contractions, ramp up duration: 0.5-3 seconds, and ramp down duration: 0.5-1.5 seconds.

Optionally, the contraction frequency may be equal to or greater than about 20 Hz, 40 Hz, 60 Hz, 80 Hz, 100 Hz, 120 Hz, 140 Hz, or 160 Hz. Optionally, the rest frequency may be equal or less than about 10 Hz, 9 Hz, 8 Hz, 7 Hz, 6 Hz, 5 Hz, 4 Hz, 3 Hz, 2 Hz, 1 Hz, or 0 Hz. Optionally, the contraction time may be equal to or greater than about 1 second, 2 seconds, 3 seconds, 4 seconds, 5 seconds, 6 seconds, 7 seconds, 8 seconds, 9 seconds, 10 seconds, 12 seconds, or 15 seconds. Optionally, the rest time may be equal to or greater than about 5 seconds, 7 seconds, 10 seconds, 12 seconds, 14 seconds, 16 seconds, 18 seconds, 20 seconds, 22 seconds, 24 seconds, 26 seconds, 28 seconds, 30 seconds, 32 seconds, 34 seconds, 36 seconds, 38 seconds, or 40 seconds. Optionally, the pulse width may be equal to or greater than about 100 uS, 125 uS, 150 uS, 175 uS, 200 uS, 225 uS, 250 uS, 275 uS, 300 uS, 325 uS, 350 uS, 375 uS, 400 uS, 425 uS, 450 uS, 475 uS, or 500 uS. Optionally, the length of stimulation may be equal to or greater than about 5 contractions, 10 contractions, 15 contractions, 20 contractions, 25 contractions, 30 contractions, 35 contractions, 40 contractions, 45 contractions, 50 contractions, 55 contractions, 60 contractions, 70 contractions, 80 contractions, 90 contractions, or 100 contractions. Optionally, the ramp up duration may be equal to or greater than about 0.1 seconds, 0.2 seconds, 0.5 seconds, 1 second, 1.5 seconds, 2 seconds, 2.5 seconds, 3 seconds, 3.5 seconds, 4 seconds, 4.5 seconds, or 5 seconds. Optionally, the ramp down duration may be equal to or greater than about 0.1 seconds, 0.2 seconds, 0.5 seconds, 1 second, 1.5 seconds, 2 seconds, 2.5 seconds, 3 seconds, 3.5 seconds, 4 seconds, 4.5 seconds, or 5 seconds. In some instances, the waveform may be periodic waveform. Optionally, the waveform may comprise a sine wave, a square wave, a triangle wave, or a sawtooth wave, or any combination thereof. The waveform may in some instances comprise composite waveforms.

In some embodiments, a stimulation program may be divided into phases or levels, and each phase or level may comprise a unique set of predefined ranges within which one or more stimulation parameters may be varied. In some embodiments, a stimulation program may comprise a single level. In some embodiments, a stimulation program may comprise 2 levels, 3 levels, 4 levels, 5 levels, 6 levels 7 levels, 8 levels, 9 levels, or 10 or more levels. In one example, a stimulation program may comprise 3 levels (e.g., a warm up level, a main level, and a cool down level). A stimulation program may comprise a plurality of levels, and each of the plurality of levels may be separately user configurable.

Figure 13:
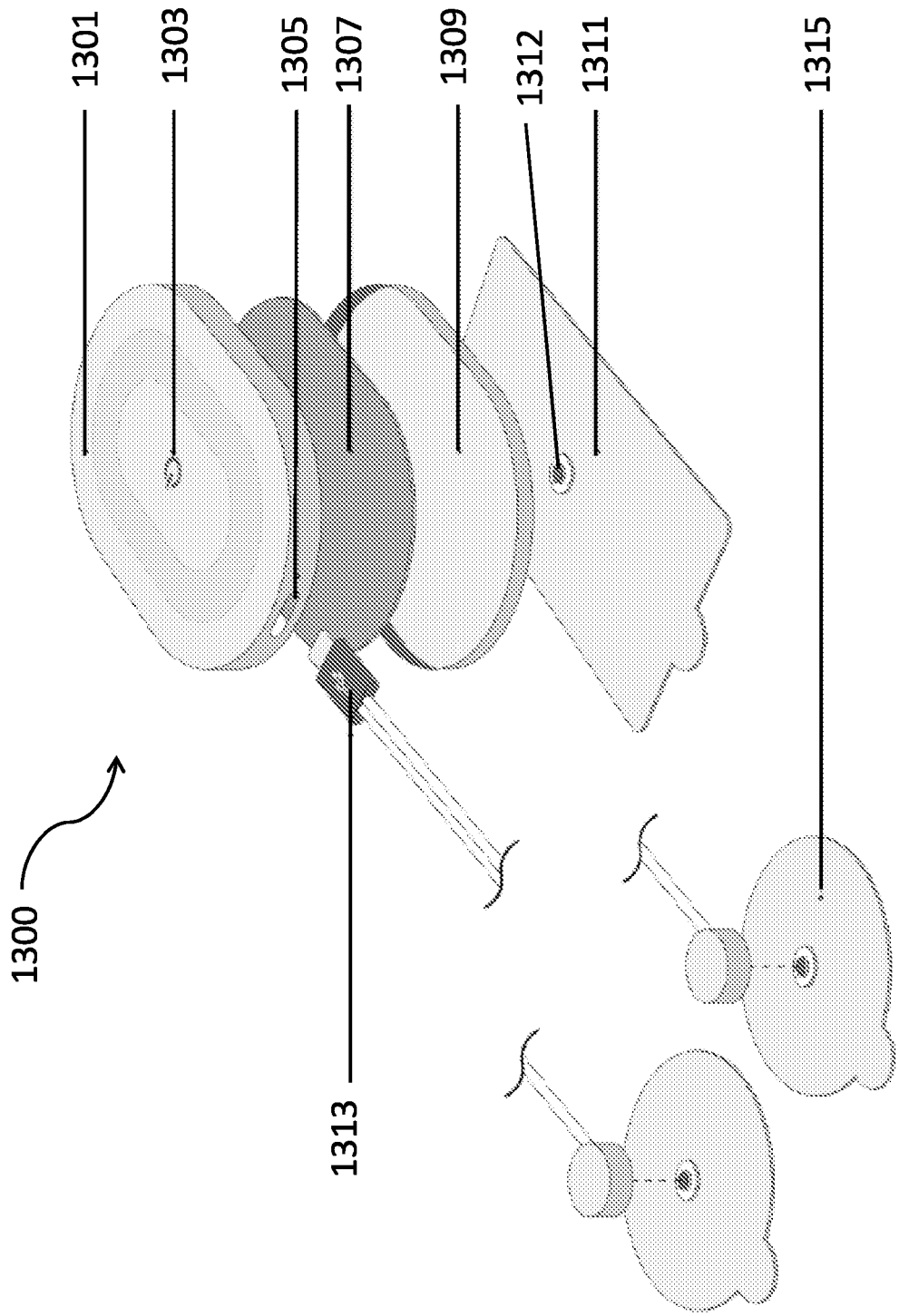
FIG. 13 illustrates a blown up view of a portable EMS device, in accordance with embodiments.

FIG. 13 illustrates a blown up view of a portable EMS device 1300, in accordance with embodiments. The device provided in FIG. 13 illustrates one embodiment of the EMS device described throughout (e.g., EMS 200 of FIG. 2). In some instances, the device may comprise, or be formed of one or more parts. For example, the device may comprise an upper casing 1301, a printed circuit board (PCB) 1307, and a bottom casing 1309. The upper casing, PCB, and the bottom casing may be coupled together to form a central body, substantially as described throughout. In some instances, the upper casing may comprise a button 1303 which may or may not be an actuatable mechanism. In some instances, the button may be a power button configured to turn the device on or off, but alternatively or in addition, may also pause or control a stimulation session.

The device may in some instances be configured to couple to an electrode 1311. In some instances, the electrode 1311 may be configured to couple to the device (e.g. bottom casing of the device) via a mating mechanism 1312. Each of the device (e.g. bottom casing of the device) and the electrode may comprise a mating mechanism. The mating mechanism may include, but are not limited to a snap on mechanism or a slide on mechanism. The mating mechanism may utilize adhesives, magnets, or may allow for form-fit coupling. The mating mechanism may allow for a permanent or temporary coupling. In some instances, the mating mechanism may enable the electrode and device to be removably coupled to one another such that the device can be removed and attached to the electrode as desired by a user.

The device may in some instances be configured to be coupled to wires and/or additional electrodes. It is to be understood that while wires 1313 and additional electrodes 1315 are shown in FIG. 13, it is not meant to be limiting. For example, the wires and additional electrodes may be unnecessary and the device may be programmed, or otherwise configured to deliver electrical impulses via electrode 1311 which is directly coupled to the device 1300. Optionally, the device may be programmed, or otherwise configured to deliver electrical impulses via both electrode 1311 and 1315. In some instances, electrical impulses may be generated on a pulse generator (e.g. on the PCB) and may be transmitted to wires (e.g. cables) via a connector 1305 such as a micro USB connector. The wires may comprise a 2 channel lead cable. The wires may couple to 1, 2, 3, 4, 5 or more electrodes, e.g. electrode 1315. In some instances, the electrode 1315 may be configured to couple to the wires via a mating mechanism. Each of the wires and the electrode may comprise a mating mechanism. The mating mechanism may include, but are not limited to a snap on mechanism or a slide on mechanism. The mating mechanism may utilize adhesives, magnets, or may allow for form-fit coupling. The mating mechanism may allow for a permanent or temporary coupling. In some instances, the mating mechanism may enable the electrode and wires to be removably coupled to one another such that the wires can be removed and attached to the electrode as desired by a user.

Figure 14:
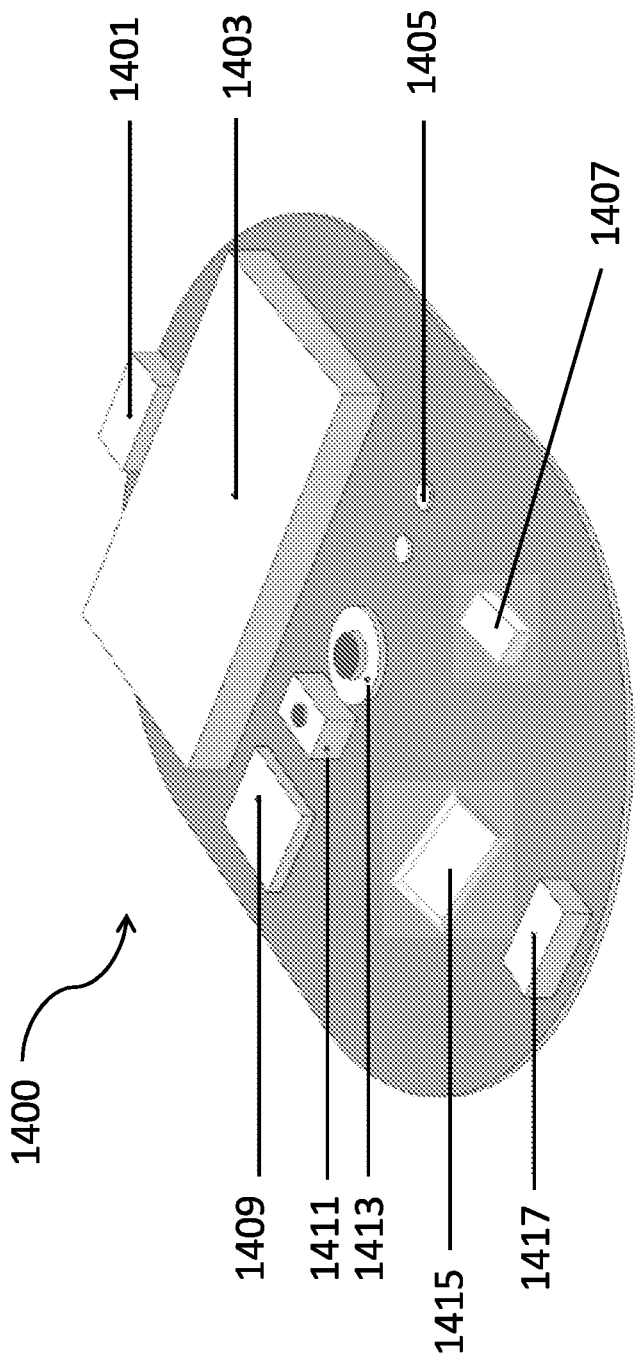
FIG. 14 illustrates components of a portable EMS device, in accordance with embodiments.

In some instances, electrical pulses generated at a PCB 1307 may be transmitted to a user. The PCB may comprise various components to enable delivery of electrical stimulation to a user. FIG. 14 illustrates components of a portable EMS device, in accordance with embodiments. In some instances, the various electronic components may be coupled to, or may be a part of a PCB 1400. The PCB 1400 may be an example of a magnified view of PCB 1307 illustrated in FIG. 13. The various electronic components coupled to the PCB (or which is part of the PCB) may include, but are not limited to, a connector (e.g. a micro USB connector) 1401 that enables connection to wires and/or electrodes, a battery 1403 that provides power to the EMS device, one or more light emitting diodes (LEDs) 1405, sensor system 1407, a pulse generator 1409, a button 1411, a mating mechanism 1413, a processing unit 1415, and a communication module 1417. Each of the components described herein may or may not be operatively coupled to one another. Each of the components described herein may or may not be electrically coupled to one another.

The various components may enable delivery of a stimulation session, electrical impulses, and/or electrical stimulation to a user. As one example, a user may designate a desired stimulation session, and/or may designate desired stimulation parameters using an application on a mobile device. For example, the user may designate a stimulation program targeted to 1) improve muscular fatigue resistance (e.g. build endurance), 2) increase muscular strength and power, 3) improve both muscular endurance and strength, 4) improve muscle recovery (e.g. through increased blood flow), or 5) potentiate muscles. Each of the stimulation sessions may comprise different stimulation parameters, substantially as described throughout. Data or signals may be generated in response to the execution of the application, and may be transmitted (e.g. wirelessly) to an EMS device. In some instances, a communication module 1417 may be programmed, or otherwise configured to receive the signals and/or data transmitted from the mobile device. The communication module may comprise any component that enables wired or wireless communication. For example, the communication module may comprise a Bluetooth chipset, an antenna, and/or radios.

The communication module may further relay the signals or data to a processing unit 1415, which may comprise one or more processors. The processing unit may in some instances comprise an application specific integrated circuit. The processing unit may in some instances process the data or signals received (e.g., via the communication module). The processing unit may optionally further execute one or more algorithms to implement a stimulation session. For example, according to the data or signals received, the processing unit may further generate or transmit signals or data to the pulse generator 1409 and/or battery 1403. The pulse generator may be programmed, or otherwise configured to generate electrical pulses corresponding to the desired stimulation session and/or parameters. For example, the pulse generator may be programmed, or otherwise configured to generate electrical impulses by accepting current from a battery or an electrical outlet. The generated pulses, or electrical impulses, may be transmitted to the connector 1401 which may be coupled to a cable, such as a 2 channel lead cable. In some instances, the connector 1401 may comprise a micro USB connector. The cable may in some instances be further coupled to electrodes. The cables may transmit the electrical pulses to the electrodes. The electrodes may further delivery the electrical stimulation, or the electrical pulses to a user to implement the stimulation session.

Optionally, the connector may be configured to be coupled to a cable to recharge the battery 1403 which provides power, or energy, to the EMS device. For example, the battery may provide power or energy to the communication module, the processing unit, the pulse generator, and/or sensor system 1407. The sensor system may be programmed, or otherwise configured to sense signals from the user. In some instances, the sensor system may be programmed, or otherwise configured to record signals from a surface of a muscle, e.g. when it is contracted. The signals may comprise mechanical and/or electrical signals. For example, a mechanomyogram (MMG), or low frequency vibration may be observed and/or recorded utilizing the sensor system. The sensor system may comprise 1, 2, 3, 4, 5, or more sensors. The sensor system may comprise any suitable approach for sensing the signals. For example, the sensor system may comprise accelerometers, gyroscopes, and/or microphones. In some instances, the accelerometer may be a 3-axis accelerometer. The sensor system may be programmed, or otherwise configured to sense signals from the user during a stimulation session. The sensor system may be programmed, or otherwise configured to sense signals from the user even in the absence of a stimulation session.

The battery may provide power in some instances to LEDs 1405. The LEDs may be utilized to provide an indication of the device to a user. The LED may be programmed, or otherwise configured to display a plurality of different colors. For example, the LED may be programmed, or otherwise configured to display different colors depending on a current status of the device, e.g., when the device is paused, recharging, running a stimulation session, running out of battery, etc. The light from the LED may in some instances be transmitted to an exterior of the EMS device via one or more light tunnels. Optionally, the light tunnels may be a part of the housing for the EMS device. For example, the light tunnels may be a part of the upper casing or lower casing described in FIG. 13.

The PCB board may further comprise a button 1411. The button may be an example of the simple interface 208 described in FIG. 2. The button may be utilized for receiving an input from a user. The button may be utilized for powering on the device and powering off the device. Alternatively or in addition, the button may be utilized for resetting the EMS device, pausing a stimulation session, resuming a stimulation session, and/or adjusting an intensity of the stimulation session.

The PCB may further comprise a mating mechanism 1413. The mating mechanism may be substantially as described with respect to FIG. 13. In some instances, the mating mechanism may enable electrical impulses to be delivered to a user. For example, the mating mechanism may allow coupling of the pulse generator with one or more electrodes, and the electrical impulses generated at the pulse generator may be delivered to a user through the mating mechanism and/or electrodes.

Computer Control Systems and Software

Figure 15:
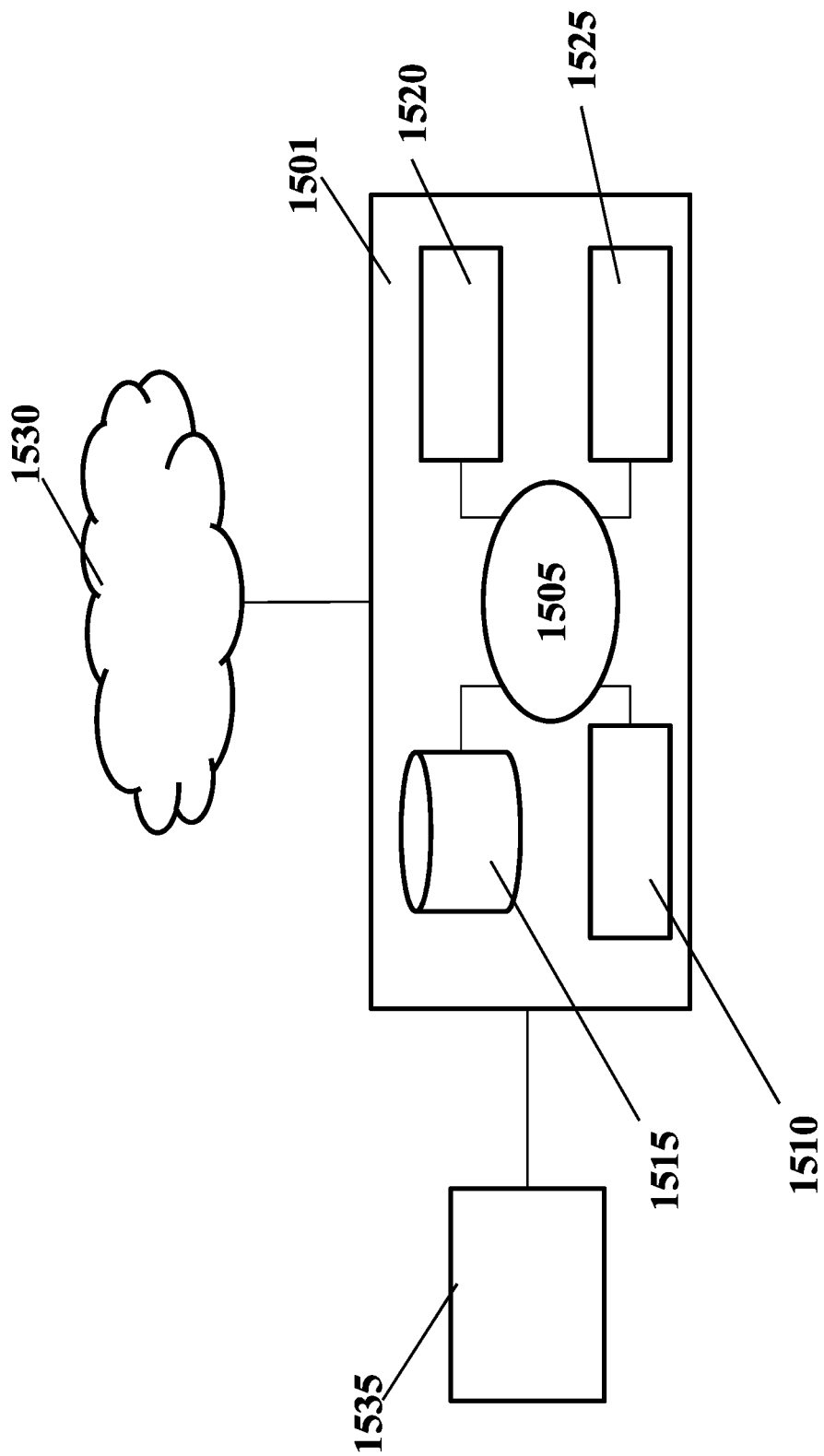
FIG. 15 illustrates a computer system that is programmed or otherwise configured to operate an electrical stimulation device.

The present disclosure provides computer control systems that are programmed to implement the methods of the disclosure. FIG. 15 shows a computer system 1501 that is programmed or otherwise configured to operate an electrical stimulation device (e.g. EMS device). The computer system 1501 can regulate various aspects of stimulation devices, systems and methods of the present disclosure, such as, for example, stimulation sessions or stimulation parameters. The computer system 1501 can execute a stimulation program. The computer system 1501 can be an electronic device of a user or a computer system that is remotely located with respect to the electronic device. The electronic device can be a mobile electronic device such as a phone, IPAD, tablet, etc.

The computer system 1501 includes a central processing unit (CPU, also "processor" and "computer processor" herein) 1505, which can be a single core or multi core processor, or a plurality of processors for parallel processing. The computer system 1501 also includes memory or memory location 1510 (e.g., random-access memory, read-only memory, flash memory), electronic storage unit 1515 (e.g., hard disk), communication interface 1520 (e.g., network adapter) for communicating with one or more other systems, and peripheral devices 1525, such as cache, other memory, data storage and/or electronic display adapters. The memory 1510, storage unit 1515, interface 1520 and peripheral devices 1525 are in communication with the CPU 1505 through a communication bus (solid lines), such as a motherboard. The storage unit 1515 can be a data storage unit (or data repository) for storing data. The computer system 1501 can be operatively coupled to a computer network ("network") 1530 with the aid of the communication interface 1520. The network 1530 can be the Internet, an internet and/or extranet, or an intranet and/or extranet that is in communication with the Internet. The network 1530 in some cases is a telecommunication and/or data network. The network 1530 can include one or more computer servers, which can enable distributed computing, such as cloud computing. The network 1530, in some cases with the aid of the computer system 1501, can implement a peer-to-peer network, which may enable devices coupled to the computer system 1501 to behave as a client or a server.

The CPU 1505 can execute a sequence of machine-readable instructions, which can be embodied in a program or software. The instructions may be stored in a memory location, such as the memory 1510. The instructions can be directed to the CPU 1505, which can subsequently program or otherwise configure the CPU 1505 to implement methods of the present disclosure. Examples of operations performed by the CPU 1505 can include fetch, decode, execute, and writeback.

The CPU 1505 can be part of a circuit, such as an integrated circuit. One or more other components of the system 1501 can be included in the circuit. In some cases, the circuit is an application specific integrated circuit (ASIC).

The storage unit 1515 can store files, such as drivers, libraries and saved programs. The storage unit 1515 can store user data, e.g., user preferences and user programs. The computer system 1501 in some cases can include one or more additional data storage units that are external to the computer system 1501, such as located on a remote server that is in communication with the computer system 1501 through an intranet or the Internet.

The computer system 1501 can communicate with one or more remote computer systems through the network 1530. For instance, the computer system 1501 can communicate with a remote computer system of a user (e.g., an athlete, healthcare service worker, or trainer). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1501 via the network 1530.

Methods as described herein can be implemented by way of machine (e.g., computer processor) executable code stored on an electronic storage location of the computer system 1501, such as, for example, on the memory 1510 or electronic storage unit 1515. The machine executable or machine readable code can be provided in the form of software. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1501 may be in communication with a stimulation (e.g., EMS) device 1535. Although one stimulation device 1535 is shown, the computer system 1501 may be in communication with a plurality of stimulation devices, e.g., as described in FIGS. 3 and 5. The stimulation device 1535 may be as described elsewhere herein (e.g., EMS 200 of FIG. 2).

The computer system 1501 can include or be in communication with an electronic display (not shown) that comprises a user interface (UI) for providing, for example, one or more controls or input elements to enable a user to control the stimulation device 1535. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1505. The algorithm may be executed in some instances once an instruction from a user is received (e.g., through the computer system 1501), and may effect operation of the stimulation device 1535. The algorithm can receive one or more signals through one or more sensors of the stimulation device 1535, and in some cases adjust the manner in which stimulation is provided to a user through the stimulation device 1535.

In some examples, the algorithm can permit the user to communicate with various application programming interfaces (API's). The algorithm can execute or implement various aspects of methods provided herein, such as the methods of FIGS. 7-9. For example, the algorithm may be executed to generate the instructions (e.g. in form of data or signals) which is then wirelessly transmitted to an EMS device. The EMS device (e.g. processing unit of the EMS device) may further process the instructions to implement or execute various aspects of the methods, such as the methods of FIGS. 7-9. Optionally, the algorithms may be executed to implement in whole, or in part, the methods of the present disclosure. For example, the algorithms may effect implementation of steps 805 through 813 of method 800 in FIG. 8.

In some instances, the algorithm may be programmed, or otherwise configured to determine or select appropriate stimulation parameters to provide an effective stimulation session. In some instances, the algorithm may be executed to provide random stimulation parameters such that a stimulation session provided to a user is better, or more efficient to achieve a desired effect (e.g., build strength, endurance, relax, potentiate muscles, etc). Optionally, the algorithm may be executed to provide further instructions to the EMS device. For example, the via execution of the algorithm, instructions may be generated that instruct a processor on board the EMS device to run a stimulation program, and a pulse generator may then generate electrical impulses in response to execution of the stimulation program, which is then transmitted to a user. As another example, via execution of the algorithm, instructions may be generated that instruct a processor on board the EMS device to broadcast a signal or command over a communication channel which is received by other EMS devices. The other EMS devices may then run a stimulation program in response to the commands, and a pulse generator of the other EMS devices may then generate electrical impulses in response to execution of the stimulation program, which is then transmitted to a user.

In some instances, the algorithms may be executed by a third party. For example, the algorithms may be executed by a healthcare provider. The healthcare may provide an input (e.g. an instruction) to a cloud based platform, which may generate an instruction that is transmitted to a user's mobile device which then executes the algorithm. Execution of the algorithm may further generate instructions that are transmitted to an EMS device. The instructions may instruct a processor on board the EMS device to run a stimulation program, and a pulse generator may then generate electrical impulses in response to execution of the stimulation program, which is then transmitted to a user.

The computer system 1501 can execute an algorithm to provide a set of stimulation instructions. Such set of stimulation instructions may be transmitted (e.g. wirelessly) to a communication module of an EMS device 1535 and be received by a processing unit (e.g., of the EMS device). The processing unit may or may not process the set of stimulations instructions and further instruct a pulse generator to generate one or more pulses for transmission to one or more electrodes or pads to deliver a stimulation session to the user. In some instances, the stimulation device 1535 may generate pulses which are delivered to a user or the stimulation device may direct pulses generated from a pulse generate to the user. The one or more pulses may include at least 1, 2, 3, 4, 5, 6, 7, 8, 9, 10, 20, 30, 40, 50, 100, 200, 300, 400, 500, 1000, or more pulses.

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A system for providing electrical stimulation to a user, the system comprising:
   a pulse generator structurally configured to generate electrical pulses in response to execution of a stimulation program;
   one or more pads in communication with the pulse generator, the one or more pads structurally configured to attach to the user and to transmit the electrical pulses to stimulate the user according to the stimulation program; and
   a processor and a memory, the memory storing non-transitory computer executable code embodied in a non-transitory computer readable medium, that, when executed by the processor, performs the steps of:
      communicating with one or more application programs linked to the user via an application programming interface, the one or more application programs including at least one of a health-related application program and a fitness-related application program;
      obtaining information regarding the user from the one or more application programs, the information related to one or more of motion of the user and health of the user;
      analyzing the information regarding the user;
      producing a tailored stimulation program for the user based on analysis of the information, the tailored stimulation program having a beginning and an end with a plurality of electrical pulses therebetween for transmitting to the user via the pulse generator, one or more of the plurality of electrical pulses including at least one of a customized pulse width and a customized duty cycle;
      presenting the tailored stimulation program alongside a plurality of predetermined stimulation programs for selection by the user, the tailored stimulation program different from the plurality of predetermined stimulation programs; and
      upon selection of the tailored stimulation program by the user, executing the tailored stimulation program with the pulse generator and the one or more pads.

2. The system of claim 1, wherein obtaining information regarding the user comprises communicating with a third-party device utilized by the user.

3. The system of claim 1, further comprising an electronic platform hosted by a server and including a web-based user interface for managing stimulation programs.

4. The system of claim 3, wherein the web-based user interface permits the user to create or manipulate a stimulation program.

5. The system of claim 4, wherein a stimulation program created by the user is retrievable by one or more different users.

6. The system of claim 3, wherein the web-based user interface provides access by the user to the tailored stimulation program and the plurality of predetermined stimulation programs for selection.

7. The system of claim 1, wherein each of the plurality of predetermined stimulation programs differ in at least one of a stimulation frequency, a pulse width, a duty cycle parameter, a ramp up and a ramp down value, and a burst pulse parameter.

8. The system of claim 1, wherein the plurality of predetermined stimulation programs include one or more of a drop foot assistance program, a rehabilitation program, a recovery program, a relaxation program, and an improved performance program.

9. The system of claim 1, wherein the information regarding the user includes a location of the user.

10. The system of claim 1, wherein the information regarding the user includes an activity of the user.

11. The system of claim 1, wherein the information regarding the user includes a physiological measurement of the user.

12. The system of claim 1, wherein the information regarding the user includes a health of the user based at least in part on one or more of a weight of the user and a body mass index (BMI) of the user.

13. The system of claim 1, wherein the computer executable code, when executed by the processor, further performs the steps of:
providing a recommendation to the user to select the tailored stimulation program; and
receiving a confirmation from the user before executing the tailored stimulation program.

14. The system of claim 1, wherein the computer executable code, when executed by the processor, further performs the steps of:
presenting, to the user, a plurality of controls for a selected stimulation program including at least pausing the selected stimulation program, resuming the selected stimulation program, increasing an intensity of the selected stimulation program, and decreasing the intensity of the selected stimulation program.

15. The system of claim 1, wherein the tailored stimulation program and the plurality of predetermined stimulation programs are made available to one or more other users in addition to the user.

16. The system of claim 15, wherein the tailored stimulation program and the plurality of predetermined stimulation programs are categorized or ranked based on one or more parameters thereof.

17. A computer-based method for providing electrical stimulation to a user, the method comprising:
communicating with one or more application programs via one or more application program interfaces (API) to obtain information on the user, the one or more application programs including at least one of a health-related application program and a fitness-related application program, wherein the information is related to one or more of motion of the user and health of the user;
analyzing the information regarding the user;
producing a tailored stimulation program for the user based on analysis of the information, the tailored stimulation program having a beginning and an end with a plurality of electrical pulses therebetween for transmitting to the user, one or more of the plurality of electrical pulses including at least one of a customized pulse width and a customized duty cycle;
presenting the tailored stimulation program alongside a plurality of predetermined stimulation programs for selection by the user, the tailored stimulation program different from the plurality of predetermined stimulation programs;
receiving a selection of a stimulation program by the user from among the presented tailored stimulation program and the plurality of predetermined stimulation programs; and
upon receiving the selection of the stimulation program by the user, executing the stimulation program, wherein executing the stimulation program comprises:
generating electrical pulses with a pulse generator according to the stimulation program; and
transmitting the electrical pulses to one or more pads attached to the user and in communication with the pulse generator thereby stimulating the user according to the stimulation program.

18. The method of claim 17, further comprising:
sending information regarding to the tailored stimulation program to the user as a recommendation; and
receiving a confirmation from the user to execute the tailored stimulation program.

19. The method of claim 17, further comprising recording the stimulation program for evaluation.

20. An electric stimulation device for stimulating a user, the electric stimulation device comprising:
a central body comprising:
a processor and a memory, the memory storing non-transitory computer executable code embodied in a non-transitory computer readable medium, that, when executed by the processor, executes a tailored stimulation program having a beginning and an end with a plurality of electrical pulses therebetween for transmitting to the user, one or more of the plurality of electrical pulses including a customized pulse width and a customized duty cycle, wherein the tailored stimulation program is created by a platform in communication with the processor in response to information regarding the user received from one or more application programs including at least one of a health-related application program and a fitness-related application program, the information related to one or more of motion of the user and health of the user;
a pulse generator structurally configured to generate the electrical pulses in response to the tailored stimulation program; and
a user interface accessible on an external surface of the central body, the user interface comprising an actuatable mechanism configured to affect a state of a stimulation program, wherein the non-transitory computer executable code, when executed by the processor, causes the user interface to present the tailored stimulation program alongside a plurality of predetermined stimulation programs for selection by the user, the tailored stimulation program different from the plurality of predetermined stimulation programs; and
one or more pads in communication with the central body, the one or more pads structurally configured to attach to the user and to transmit the electrical pulses to stimulate the user according to the state of the stimulation program.

* * * * *